(12) United States Patent
Mehrotra et al.

(10) Patent No.: US 11,975,024 B2
(45) Date of Patent: May 7, 2024

(54) T REGULATORY (TREG) CELL TRANSPLANTATION IN OSTEOGENESIS IMPERFECTA (OI)

(71) Applicant: MUSC Foundation for Research Development, Charleston, SC (US)

(72) Inventors: Meenal Mehrotra, Mount Pleasant, SC (US); In-Hong Kang, Charleston, SC (US); Uday Baliga, Charleston, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 965 days.

(21) Appl. No.: 16/772,967

(22) PCT Filed: Dec. 17, 2018

(86) PCT No.: PCT/US2018/065912
§ 371 (c)(1),
(2) Date: Jun. 15, 2020

(87) PCT Pub. No.: WO2019/125981
PCT Pub. Date: Jun. 27, 2019

(65) Prior Publication Data
US 2021/0161956 A1 Jun. 3, 2021

Related U.S. Application Data

(60) Provisional application No. 62/607,386, filed on Dec. 19, 2017.

(51) Int. Cl.
*A61K 35/17* (2015.01)
*A61K 35/28* (2015.01)
*A61K 45/06* (2006.01)
*A61P 19/08* (2006.01)
*C12N 5/0783* (2010.01)

(52) U.S. Cl.
CPC .............. *A61K 35/17* (2013.01); *A61K 35/28* (2013.01); *A61K 45/06* (2013.01); *A61P 19/08* (2018.01); *C12N 5/0637* (2013.01); *C12N 2501/15* (2013.01); *C12N 2501/2302* (2013.01); *C12N 2501/998* (2013.01); *C12N 2501/999* (2013.01)

(58) Field of Classification Search
None
See application file for complete search history.

(56) References Cited

U.S. PATENT DOCUMENTS

| 8,961,956 | B2 | 2/2015 | Kimbrel | |
| 2009/0257988 | A1* | 10/2009 | Horwitz | C12N 5/0636 435/375 |
| 2011/0027278 | A1 | 2/2011 | Noelle | |
| 2011/0268752 | A1* | 11/2011 | Riley | A61K 39/0008 435/375 |
| 2012/0315282 | A1 | 12/2012 | Bedinger | |
| 2013/0267463 | A1 | 10/2013 | Youn | |
| 2015/0232880 | A1 | 8/2015 | Hemminki | |
| 2016/0193180 | A1 | 7/2016 | Cho | |
| 2016/0220567 | A1 | 8/2016 | Park | |
| 2016/0304579 | A1 | 10/2016 | Toporik | |

FOREIGN PATENT DOCUMENTS

| WO | 2016196774 A1 | 12/2016 |
| WO | 2017072344 A1 | 5/2017 |
| WO | 2017152102 A2 | 9/2017 |

OTHER PUBLICATIONS

Toben et al, 2011, "Fracture Healing is Accelerated in the Absence of the Adaptive Immune System." J Bone Miner Res, 26(1):113-24.
Nam et al, 2012, "T-Lymphocytes Enable Osteoblast Maturation via IL-17F during hte Early Phase of Fracture Repair." PLoS One, 7(6):e40044.
Reinke et al, 2013, "Terminally Differentiated CD8+ T Cells Negatively Affect Bone Regeneration in Humans." Sci Transl Med, 5(177):177ra36.
Konnecke et al, 2014, "T and B cells participate in bone repair by infiltrating the fracture callus in a two-wave fashion." Bone, 64:155-65.
Liu et al, 2011, "Mesenchymal sem cell-based tissue regeneration is governed by recipient T lymphocytes via IFN-gama and TNF-alpha." Nat Med, 17(12):1594-601.
Zaiss et al, 2010, "Increased Bone Density and Resistance to Ovariectomy-Induced Bone Loss in FoxP3-Transgenic Mice Based on Impaired Osteoclast Differentiation." Arthritis Rheum, 62(8):2328-38.
Talaat et al, 2015, "Effect of bisphosphonates treatment on cytokine imbalance between TH17 and Treg in osteoporosis." Inflammopharmacology, 23(2-3):119-25.
Zhao et al., 2012, "Bone marrow and the control of immunity." Cell Mol Immunol, 9(1): 11-19.
Kang et al., 2017, "Efficacy of Regulatory T Cell Transplantation in a Mouse Model of Osteogenesis Imperfecta." Journal of Bone and Mineral Research, 32: S285-S285.

* cited by examiner

*Primary Examiner* — Daniel C Gamett
(74) *Attorney, Agent, or Firm* — Riverside Law LLP

(57) ABSTRACT

The present invention relates to compositions comprising induced T regulatory cells (iTregs), methods of making the compositions, and methods of using the compositions for enhancing bone remodeling in the treatment of Osteogenesis Imperfecta (OI).

17 Claims, 24 Drawing Sheets

Clinical presentation of OI

Radiograph of the leg (two projections): Curved, thin bones with diminished bone density (arrows) and fracture of the middle third of the tibia (double arrow) are visible.

Shortened ribs and fractures in the forearm

1. LIF
2. CCL3/CCL4; 3. Cystatin C; 4. Flt-3 ligand; 5. Osteopontin
6. CCL5; 7. IL-17A

T REGULATORY (TREG) CELL TRANSPLANTATION IN OSTEOGENESIS IMPERFECTA (OI)

CROSS-REFERENCE TO RELATED APPLICATIONS

This application is the U.S. national phase application filed under 35 U.S.C. § 371 claiming benefit to International Patent Application No. PCT/US2018/065912, filed Dec. 17, 2018, which is entitled to priority under 35 U.S.C. § 119(e) to U.S. Provisional Patent Application No. 62/607,386, filed Dec. 19, 2017, each of which application is hereby incorporated herein by reference in its entirety.

STATEMENT REGARDING FEDERALLY SPONSORED RESEARCH OR DEVELOPMENT

This invention was made with government support under NIH/NIAMS R01 AR066094 awarded by the National Institutes of Health (NIH), and K01AR059097 awarded by the National Institute of Arthritis and Musculoskeletal and Skin Diseases (NIAMS). The government has certain rights in the invention.

BACKGROUND OF THE INVENTION

Osteogenesis imperfecta (OI), the most common hereditary bone disease, is characterized by a reduction in the quantity of bone matrix that leads to repeated fractures and bone deformity. It is often called "brittle bone disease". The incidence of OI in the United States is estimated to be 1 per 20,000 live births, but there is no cure at present. The goals of therapy for patients with OI are to reduce fracture rates, prevent bone deformities and minimize chronic pain while maximizing bone health. Long-term treatment with drugs has undesired side effects; therefore, alternative strategies are needed to enhance bone remodeling.

Therefore, there is a need in the art for improved therapies for OI, including strategies to enhance bone remodeling. The present invention addresses this unmet need.

SUMMARY OF THE INVENTION

In one aspect, the invention provides a composition for enhancing bone remodeling, or for treating osteogenesis imperfecta (OI), comprising at least one selected from the group consisting of: an induced T regulatory cell (iTreg), and iTreg conditioned medium (CM).

In one embodiment, the composition further comprises at least one bone marrow (BM) cell.

In one embodiment, the iTreg is made by a method comprising incubating CD4$^+$ spleen cells with a composition comprising at least one selected from the group consisting of: anti-CD3 antibody, anti-CD28 antibody, IL-2, TGF-β, and retinoic acid.

In one embodiment, the iTreg is made by a method comprising incubating CD4$^+$ spleen cells with a composition comprising anti-CD3 antibody, anti-CD28 antibody, IL-2, TGF-β, and retinoic acid In one embodiment, the incubating step lasts for at least about three days.

In one embodiment, the incubating step lasts for between about three days and about five days.

In one embodiment, the iTreg exhibits elevated expression of at least FoxP3.

In one embodiment, the CM is made by a method comprising incubating one or more iTregs with serum free media.

In one embodiment, the incubating step lasts for at least about 12 hours.

In one embodiment, the incubating step lasts for at least about 24 hours.

In one embodiment, the composition further comprises at least one additional agent used to treat OI.

In one embodiment, the additional agent comprises a bisphosphonate.

In one embodiment, the bisphosphonate comprises at least one selected from the group consisting of: cholecalciferol, zoledronic acid, calcium carbonate, pamidronate, neridronate, olpadronate, alendronate, ibandronate, risedronate, zoledronate, etidronate, clodronate, and tiludronate.

In one embodiment, the additional agent comprises at least one agent selected from the group consisting of: clomifene, raloxifene, tamoxifen, toremifene, bazedoxifene, lasofoxifene, ormeloxifene, Odanacatib, a Vitamin D analog, Denosumab, recombinant growth hormone, Romosozumab, Blosozumab, BSP804, Teriparatide, SD-208, ID11, Fresolimumab, and a combination thereof.

In another aspect, the invention provides a composition for enhancing the formation of at least one iTreg, comprising at least one agent selected from the group consisting of: anti-CD3 antibody, anti-CD28 antibody, IL-2, TGF-β, and retinoic acid. In one embodiment, the composition comprises anti-CD3 antibody, anti-CD28 antibody, IL-2, TGF-β, and retinoic acid.

In another aspect, the invention provides a method for enhancing bone remodeling, or for treating osteogenesis imperfecta (OI), comprising administering to a subject a composition of the invention.

In one embodiment, the method further comprises the step of administering at least one BM cell to the subject.

In one embodiment, the composition of the method further comprises at least one BM cell.

In one embodiment, the iTreg is made by incubating CD4$^+$ spleen cells with a composition comprising at least one selected from the group consisting of: anti-CD3 antibody, anti-CD28 antibody, IL-2, TGF-β, and retinoic acid.

In one embodiment, the iTreg is made by incubating CD4$^+$ spleen cells with a composition comprising anti-CD3 antibody, anti-CD28 antibody, IL-2, TGF-β, and retinoic acid.

In one embodiment, the incubating step lasts for at least about three days.

In one embodiment, the incubating step lasts for between about three days and about five days.

In one embodiment, the iTreg exhibits elevated expression of at least FoxP3.

In one embodiment, the CM is made by a method comprising incubating one or more iTregs with serum free media.

In one embodiment, the incubating step lasts for at least about 12 hours.

In one embodiment, the incubating step lasts for at least about 24 hours.

In one embodiment, the method further comprises the step of administering at least one additional agent used to treat OI to the subject.

In one embodiment, the additional agent comprises a bisphosphonate.

In one embodiment, the bisphosphonate comprises at least one selected from the group consisting of: cholecalciferol, zoledronic acid, calcium carbonate, pamidronate, neridronate, olpadronate, alendronate, ibandronate, risedronate, zoledronate, etidronate, clodronate, and tiludronate.

In one embodiment, the additional agent comprises at least one agent selected from the group consisting of: clomifene, raloxifene, tamoxifen, toremifene, bazedoxifene, lasofoxifene, ormeloxifene, Odanacatib, a Vitamin D analog, Denosumab, recombinant growth hormone, Romosozumab, Blosozumab, BSP804, Teriparatide, SD-208, ID11, Fresolimumab, and a combination thereof.

In one embodiment, the composition further comprises at least one additional agent used to treat OI.

In one embodiment, the additional agent comprises a bisphosphonate.

In one embodiment, the bisphosphonate comprises at least one selected from the group consisting of: cholecalciferol, zoledronic acid, calcium carbonate, pamidronate, neridronate, olpadronate, alendronate, ibandronate, risedronate, zoledronate, etidronate, clodronate, and tiludronate.

In one embodiment, the additional agent comprises at least one agent selected from the group consisting of: clomifene, raloxifene, tamoxifen, toremifene, bazedoxifene, lasofoxifene, ormeloxifene, Odanacatib, a Vitamin D analog, Denosumab, recombinant growth hormone, Romosozumab, Blosozumab, BSP804, Teriparatide, SD-208, ID11, Fresolimumab, and a combination thereof.

In another aspect, the invention provides a composition for inducing the formation of iTregs, comprising at least one agent selected from the group consisting of: anti-CD3 antibody, anti-CD28 antibody, IL-2, TGF-β, and retinoic acid.

In one embodiment, the composition comprises anti-CD3 antibody, anti-CD28 antibody, IL-2, TGF-β, and retinoic acid.

In one embodiment, the anti-CD3 antibody is present at a concentration of between 1 μg/mL and 10 μg/mL, the anti-CD28 antibody is present at a concentration of between 1 μg/mL and 10 μg/mL, the IL-2 is present at a concentration of between 20 U/mL and 200 U/mL, the TGF-β is present at a concentration of between 1 ng/mL and 10 ng/mL, and the retinoic acid is present at a concentration of between 8 nmol/mL and 80 nmol/mL.

In one embodiment, the anti-CD3 antibody is present at a concentration of 5 μg/mL, the anti-CD28 antibody is present at a concentration of 5 μg/mL, the IL-2 is present at a concentration of 100 U/mL, the TGF-β is present at a concentration of 5 μg/mL, and the retinoic acid is present at a concentration of 40 nmol/mL.

BRIEF DESCRIPTION OF THE DRAWINGS

The following detailed description of embodiments of the invention will be better understood when read in conjunction with the appended drawings. It should be understood that the invention is not limited to the precise arrangements and instrumentalities of the embodiments shown in the drawings.

FIG. 2A and FIG. 2B, depicts results from example experiments, demonstrating the activated phenotype of T cells as well as enhanced cytokine secretion by T cells in oim mice. (FIG. 2A) Spleen derived naïve T cells from WT and oim mice were stained using fluorochrome conjugated antibody for various cell surface molecules, and analysis was performed after acquiring the samples in FACS and analyzed using FlowJo software. Data from one of three experiments with similar results is shown. Naïve splenic T cells obtained from OI mice exhibited relatively higher expression of activation molecule CD44, indicating their activated phenotype. (FIG. 2B) Splenic T cells from WT and oim mice were activated for three days using anti-CD3 (5 μg/mL) and anti-CD28 antibody (5 μg/mL) before being re-stimulated with similar stimuli in presence of Golgi-Plug. Intracellular staining was done with fluorochrome conjugated anti-cytokine antibody, and data was acquired using FACS. Upper panel represents IFN-γ and lower panel is from TNF-α secretion. The numerical values within each display are mean fluorescence intensity (MFI). The dotted vertical line indicates the mean position of the peak in WT T cells to visually compare the relative expression between samples. Data from one of three experiments with similar results is shown. There is a greater expression of both IFN-γ and TNF-α in OI T cells as compared to WT T cells.

FIG. 8A through FIG. 8H, depicts results from example experiments, demonstrating the morphometric comparison of tibia from oim transplanted with BM from another oim mice (OI-OI), oim transplanted with WT BM only and oim transplanted with WT BM+WT iTregs. To determine in vivo functionality of iTregs, oim mice were transplanted with total BM cells with and without iTregs and the changes in bone morphology tracked by Micro-CT 3-4 months after transplantation. The increase in bone volume/total volume (FIG. 8A) and trabecular number (FIG. 8B) observed in oim mice transplanted with WT BM+iTregs was significantly greater than the increase observed with BM transplantation only. A concomitant significantly greater decrease in trabecular spacing (FIG. 8D) was also observed. Trabecular pattern factor also showed a greater decrease, indicating improvement in connectivity and structure of trabeculae (FIG. 8E). There was a significant increase in trabecular thickness (FIG. 8C) in the BM+iTreg transplanted group only. Cortical width also showed a significant increase after BM and BM+iTreg transplantation (FIG. 8F). This can also be appreciated in the representative images of the trabecular bone (left panel) and the cortical bone (right panel) (FIG. 8G). (*p<0.05 BM or BM+iTreg versus OI-OI; #p<0.05 BM+iTreg versus BM only). FIG. 8H depicts the results of mechanical testing of the bone. After micro-CT, femurs were mechanically tested in 3-point bending using an electroforce system (ELF3200, EnduraTec) with a custom testing apparatus to test the femurs to failure at a constant displacement rate of 0.025 mm/s. Analysis revealed that there was an increase in stiffness of the OI bone after BM and BM+iTreg transplantation. There was also an increase in the maximum displacement for the same maximum load in the OI bone after BM and BM+iTreg transplantation.

To determine if auto-transplantation would be beneficial, oim mice were transplanted with total BM cells from another oim mice±iTregs from another oim mice and the changes in bone morphology were tracked by Micro-CT 6 months after transplantation. FIG. 11E shows improved mechanical properties in oim mouse transplanted with oim BM+oim iTregs as compared to oim BM only. Femurs were mechanically tested in 3-point bending using an electroforce system (ELF3200, EnduraTec) with a custom testing apparatus to test the femurs to failure at a constant displacement rate of 0.025 mm/s. Analysis revealed that there was a significant increase in stiffness, maximum load and maximum stiffness in oim mouse transplanted with oim BM+oim iTregs as compared to oim BM only; *p<0.05.

FIG. 12A and FIG. 12B, depicts results from example experiments, demonstrating the in vitro culture of oim calvarial cells with conditioned media (CM) from WT and OI iTregs. To obtain CM, after generating iTregs, the cells were washed and incubated with serum free media for 24 hours, which was then collected, centrifuged and stored at −80° C. until needed. To determine the effect of Tregs on osteogenesis, oim calvarial cells were cultured in osteogenic media ($\alpha$-MEM/15% FBS/ascorbic acid/$\beta$-glycerophosphate) supplemented with 50% CM from iTregs. There was an increase in mineralization, as seen by alizarin red staining (FIG. 12A) when the oim calvarial cells were treated with WT as well as OI iTreg CM as compared to cells grown with no CM. This increase was significant as is evident by quantification of the alizarin red staining (FIG. 12B). This indicates that iTregs have an effect on osteoblasts in OI and also that oim iTreg CM showed similar effects to WT iTreg CM. *p<0.05 WT and oim iTreg CM versus control media.

FIG. 13A and FIG. 13B, depicts results from example experiments, demonstrating the in vitro culture of oim bone marrow cells for osteoclastogenesis with CM from WT and OI iTregs. To determine the effects of Tregs on osteoclastogenesis, BM was harvested from the tibia and femur of 4-5 week old oim mice. The cells were seeded into a 100 mm dish in $\alpha$-MEM with 10% FBS and incubated at 37° C. overnight. The supernatant was collected next day and centrifuged to collect the non-adherent BM cells, which were plated in 24 well dishes at $10 \times 10^6$ cells per well in $\alpha$-MEM/10% FBS/RANKL/M-CSF supplemented with 50% CM from iTregs. The cells were stained for TRAP using leukocyte acid phosphatase kit to assess for formation of multinucleated TRAP$^+$ osteoclasts. There was a significant reduction in the number of osteoclasts formed when the BM cells were treated with CM from WT and OI iTregs, as seen both in the images (FIG. 13A) and in the quantification of the osteoclast numbers (FIG. 13B). This indicates that iTregs have an effect on osteoclasts in OI and also that oim iTreg CM showed similar effects to WT iTreg CM. *p<0.05 WT and oim iTreg CM versus control media.

DETAILED DESCRIPTION

Figure 1:
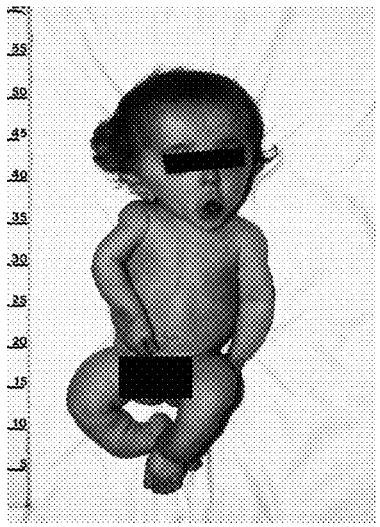
FIG. 1 depicts clinical presentation of Osteogenesis Imperfecta (OI). OI is a brittle bone disease, with an incidence of 1 in 15-20,000 live births. OI is also referred to as a "Collagen-related disorder" as OI can be caused by mutations in Type I collagen (Classical OI; autosomal dominant) as well as mutations in non-collagenous genes whose protein products interact with collagen (Non-classical; Autosomal recessive). There is presently no cure for OI, only symptomatic treatment.
Figure 1:
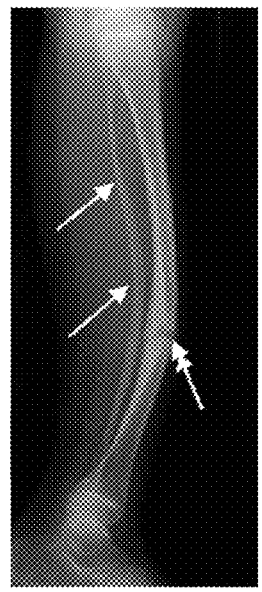
Figure 1:

The present invention relates to the discovery that administering a composition comprising a bone marrow (BM) cell and an induced T regulatory (iTreg) cell is an effective therapy for enhancing bone remodeling in skeletal diseases and disorders, such as osteogenesis imperfecta (OI).

The present invention also relates to the discovery that administering a composition comprising T regulatory cells (Treg) in the absence of bone marrow cells is an effective therapy for enhancing bone remodeling in skeletal diseases and disorders, such as osteogenesis imperfecta (OI). In some instances, the Treg can be iTregs.

In one embodiment, the cells of the invention can be autologous, allogenic or xenogenic to the transplant recipient.

The invention also relates to the discovery that one or more factors secreted by an iTreg cell, in the form of conditioned media, can promote osteogenesis. The invention relates to compositions and methods for enhancing bone remodeling in the context of skeletal diseases and disorders, such as OI.

The invention provides a composition for enhancing bone remodeling or for treating OI, comprising at least one iTreg, iTreg conditioned medium (CM), or at least one iTreg combined with iTreg CM. The composition may further comprise a BM cell. The composition may further comprise one or more additional agents used for the treatment of OI. These additional agents may include, for example, one or more bisphosphonates. The one or more bisphosphonates may be, for example, at least one of cholecalciferol, zoledronic acid, calcium carbonate, pamidronate, neridronate, olpadronate, alendronate, ibandronate, risedronate, zoledronate, etidronate, clodronate, and tiludronate. Other agents may include SERM such as tamoxifen, Cathepsin K inhibitors such as Odanacatib, Vitamin D analogues, RANKL monoclonal antibody such as Denosumab, recombinant growth hormone, sclerostin antibody such as Romosozumab, Blosozumab, BSP804, recombinant human PTH such as Teriparatide and TGF-β inhibitors such as SD-208, ID11, and Fresolimumab. In one embodiment, the iTreg is derived from a donor who is different than the recipient, for an allogeneic transplantation. In one embodiment, the iTreg is derived from the subject who is also the recipient, for an autologous transplantation. Alternatively, the cells can be allogeneic, syngeneic or xenogeneic with respect to the recipient.

The invention also provides a composition for producing an iTreg cell. In one embodiment, the composition comprises at least one selected from the group including: anti-CD3 antibody, anti-CD28 antibody, IL-2 protein, TGF-β protein, and retinoic acid. In one embodiment, the composition comprises anti-CD3 antibody, anti-CD28 antibody, IL-2 protein, TGF-β protein, and retinoic acid. In one embodiment, the iTreg is produced outside of the subject (i.e., ex vivo).

The invention provides a composition for producing or stimulating an iTreg cell inside a subject, for enhancing bone remodeling, or for treating OI. The invention also provides a composition for increasing the number of Tregs in a subject, for enhancing bone remodeling, or for treating OI. Methods of the invention for increasing the number of iTregs and/or Tregs in a subject may utilize the compositions intended for this purpose. An exemplary compound that may be used to increase the number of iTregs and/or Tregs in a subject, and which may also be used for enhancing bone remodeling, or for treating OI, includes, but is not limited to, a PPAR-gamma agonist such as Thiazolidinedione (TZD). In one embodiment, the iTreg is produced inside of the subject (i.e., in vivo).

The invention also provides a method for enhancing bone remodeling, or for treating OI, by increasing one or more biological activities of a Treg or iTreg cell. In one embodiment, a method for enhancing bone remodeling, or for treating OI, comprises administering to a subject a composition for enhancing bone remodeling, or for treating OI, comprising at least one iTreg, iTreg CM, or at least one iTreg combined with iTreg CM. In one embodiment, the method further comprises administering at least one BM cell to the subject. In one embodiment, the composition of the method further comprises at least one BM cell. In one embodiment, the method further comprises administering at least one additional agent for enhancing bone remodeling, or for treating OI, to the subject. In one embodiment, the composition of the method further comprises at least one additional agent for treating OI. These additional agents may include, for example, one or more bisphosphonates. The one or more bisphosphonates may be, for example, at least one of cholecalciferol, zoledronic acid, calcium carbonate, pamidronate, neridronate, olpadronate, alendronate, ibandronate, risedronate, zoledronate, etidronate, clodronate, and tiludronate. Other agents may include SERM such as tamoxifen, Cathepsin K inhibitors such as Odanacatib, Vitamin D analogues, RANKL monoclonal antibody such as Denosumab, recombinant growth hormone, sclerostin antibody such as Romosozumab, Blosozumab, BSP804, recombinant human PTH such as Teriparatide and TGF-β inhibitors such as SD-208, ID11, and Fresolimumab.

The invention also provides a method for producing an iTreg cell. In one embodiment, the iTreg cell is derived from a CD4$^+$ spleen cell. In one embodiment, the CD4$^+$ spleen cell is cultured in the presence of at least one selected from the group including: anti-CD3 antibody, anti-CD28 antibody, IL-2 protein, TGF-β protein, and retinoic acid. In one embodiment, the CD4$^+$ spleen cell is cultured in the presence of anti-CD3 antibody, anti-CD28 antibody, IL-2 protein, TGF-β protein, and retinoic acid. In one embodiment, the CD4$^+$ spleen cell is cultured in the presence of between 1 μg/mL and 10 μg/mL of anti-CD3 antibody, between 1 μg/mL and 10 μg/mL of anti-CD28 antibody, between 20 U/mL and 200 U/mL of IL-2 protein, between 1 ng/mL and 10 ng/mL of TGF-β protein, and between 8 nmol/mL and 80 nmol/mL of retinoic acid. In one embodiment, the CD4$^+$ spleen cell is cultured in the presence of 5 μg/mL of anti-CD3 antibody, 5 μg/mL of anti-CD28 antibody, 100 U/mL of IL-2 protein, 5 μg/mL of TGF-β protein, and 40 nmol/mL of retinoic acid.

Definitions

Unless defined otherwise, all technical and scientific terms used herein have the same meaning as commonly understood by one of ordinary skill in the art to which this invention belongs.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

As used herein, to "alleviate" a disease means reducing the severity of one or more symptoms of the disease.

As used herein, the term "autologous" is meant to refer to any material derived from the same subject to which it is later to be re-introduced into the subject.

"Allogeneic" refers to a graft derived from a different animal of the same species.

"Xenogeneic" refers to a graft derived from an animal of a different species.

"Alloantigen" is an antigen that differs from an antigen expressed by the recipient.

The term "antibody" as used herein, refers to an immunoglobulin molecule, which is able to specifically bind to a specific epitope on an antigen. Antibodies can be intact immunoglobulins derived from natural sources or from recombinant sources and can be immunoactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab).sub.2, as well as single chain antibodies and humanized antibodies (Harlow et al., 1988; Houston et al., 1988; Bird et al., 1988).

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequence or a partial nucleotide sequence encoding a protein that elicits an immune response therefore encodes an "antigen" as that term is used herein. Furthermore, one skilled in the art will understand that an antigen need not be encoded solely by a full-length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

"An antigen presenting cell" (APC) is a cell that is capable of activating T cells, and includes, but is not limited to, monocytes/macrophages, B cells and dendritic cells (DCs).

The term "dendritic cell" or "DC" refers to any member of a diverse population of morphologically similar cell types found in lymphoid or non-lymphoid tissues. These cells are characterized by their distinctive morphology, high levels of surface MHC-class II expression. DCs can be isolated from a number of tissue sources. DCs have a high capacity for sensitizing MHC-restricted T cells and are very effective at presenting antigens to T cells in situ. The antigens may be self-antigens that are expressed during T cell development and tolerance, and foreign antigens that are present during normal immune processes.

As used herein, the term "autologous" is meant to refer to any material derived from the same individual to which it is later to be re-introduced into the mammal.

A "disease" is a state of health of an animal wherein the animal cannot maintain homeostasis, and wherein if the disease is not ameliorated, then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "DNA" as used herein is defined as deoxyribonucleic acid. "Donor antigen" refers to an antigen expressed by the donor tissue to be transplanted into the recipient.

"Recipient antigen" refers to a target for the immune response to the donor antigen.

As used herein, an "effector cell" refers to a cell which mediates an immune response against an antigen. An example of an effector cell includes, but is not limited to a T cell and a B cell.

"Mixed lymphocyte reaction," "mixed lymphocyte culture," "MLR," and "MLC" are used interchangeably to refer to a mixture comprising a minimum of two different cell populations that are allotypically different. At least one of the allotypically different cells is a lymphocyte. The cells are cultured together for a time and under suitable conditions to result in the stimulation of the lymphocytes, e.g., Treg cells. A frequent objective of an MLC is to provide allogeneic stimulation, such as may initiate proliferation of the Treg cells; but unless indicated, proliferation during the culture is not required. In the proper context, these terms may alternatively refer to a mixture of cells derived from such a culture. When cells from an MLC are administered as a bolus to a human, it is referred to as a "cellular implant."

As used herein "endogenous" refers to any material from or produced inside an organism, cell, tissue or system.

By the term "effective amount", as used herein, is meant an amount that when administered to a mammal, causes a detectable level of immune suppression or tolerance compared to the immune response detected in the absence of the composition of the invention. The immune response can be readily assessed by a plethora of art-recognized methods. The skilled artisan would understand that the amount of the composition administered herein varies and can be readily determined based on a number of factors such as the disease or condition being treated, the age and health and physical condition of the mammal being treated, the severity of the disease, the particular compound being administered, and the like.

As used herein, the term "exogenous" refers to any material introduced from or produced outside an organism, cell, tissue or system.

The term "epitope" as used herein is defined as a small chemical molecule on an antigen that can elicit an immune response, inducing B and/or T cell responses. An antigen can have one or more epitopes. Most antigens have many epitopes; i.e., they are multivalent. In general, an epitope is roughly about 10 amino acids and/or sugars in size. For example, the epitope may be about 4-18 amino acids, about 5-16 amino acids, about 6-14 amino acids, about 7-12 amino acids, or about 8-10 amino acids. One skilled in the art understands that generally the overall three-dimensional structure, rather than the specific linear sequence of the molecule, is the main criterion of antigenic specificity and therefore distinguishes one epitope from another. Based on the present disclosure, a peptide of the present invention can be an epitope.

The term "expression" as used herein is defined as the transcription and/or translation of a particular nucleotide sequence driven by its promoter.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, siRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

The term "helper T cell" as used herein is defined as an effector T cell whose primary function is to promote the activation and functions of other B and T lymphocytes and or macrophages. Helper T cells may be CD4 T-cells.

The term "heterologous" as used herein is defined as DNA or RNA sequences or proteins that are derived from different species.

As used herein, "homology" is used synonymously with "identity."

The term "immunoglobulin" or "Ig", as used herein is defined as a class of proteins, which function as antibodies. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most mammals. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

The term "immunostimulatory" is used herein to refer to increasing overall immune response.

The term "immunosuppressive" is used herein to refer to reducing overall immune response.

"Initiating iTreg conversion" as used herein refers to any event which results in a detectable increase in the phenotype and/or genotype characteristic of T regulatory cells. For example, a phenotype and/or genotype characteristic of T regulatory cell is CD25 expression thus resulting in the generation of $CD4^+$ $CD25^+$ cells from $CD4^+$ $CD25^-$ cells. Another phenotype and/or genotype characteristic of T regulatory cell is immunosuppression.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

The term "polypeptide" as used herein is defined as a chain of amino acid residues, usually having a defined sequence. As used herein the term polypeptide is mutually inclusive of the terms "peptide" and "protein".

The term "self-antigen" as used herein is defined as an antigen that is expressed by a host cell or tissue. Self-antigens may be tumor antigens, but in certain embodiments, are expressed in both normal and tumor cells. A skilled artisan would readily understand that a self-antigen may be overexpressed in a cell.

As used herein, "specifically binds" refers to the fact that a first compound binds with a second compound, and does not bind in a significant amount to other compounds present in a mixture or sample.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cells that have been separated from the cells with which they are naturally associated in their natural state. In some embodiments, the cells are cultured in vitro. In other embodiments, the cells are not cultured in vitro.

As the term is used herein, "substantially separated from" or "substantially separating" refers to the characteristic of a population of first substances being removed from the proximity of a population of second substances, wherein the population of first substances is not necessarily devoid of the second substance, and the population of second substances is not necessarily devoid of the first substance. However, a population of first substances that is "substantially separated from" a population of second substances has a measurably lower content of second substances as compared to the non-separated mixture of first and second substances.

A "population" is used herein to refer to a group of cells having a substantially similar phenotypic characteristic.

"Transplant" refers to a biocompatible lattice or a donor tissue, organ or cell, to be transplanted. An example of a transplant may include but is not limited to skin cells or tissue, bone marrow, induced T regulatory cells (iTregs), and solid organs such as heart, pancreas, kidney, lung, and liver. A transplant can also refer to any material that is to be administered to a host. For example, a transplant can refer to a nucleic acid or a protein.

The term "T-cell" as used herein is defined as a thymus-derived cell that participates in a variety of cell-mediated immune reactions.

The term "B-cell" as used herein is defined as a cell derived from the bone marrow and/or spleen. B cells can develop into plasma cells which produce antibodies.

As used herein, a "therapeutically effective amount" is the amount of a therapeutic composition sufficient to provide a beneficial effect to a mammal to which the composition is administered.

As used herein, "treating" refers to the reduction, alleviation or elimination, for example, to normal levels, of one or more of the symptoms of the disease or condition which is being treated, e.g. alleviation of osteogenesis imperfecta, relative to the symptoms prior to treatment. As used herein "treating" or "treatment" includes both therapeutic and prophylactic treatments.

The term "vaccine" as used herein is defined as a material used to provoke an immune response after administration of the material to a mammal.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Xenogeneic" refers to a graft derived from an animal of a different species.

As used herein, the term "CD4" refers to a cell-surface glycoprotein typically found on the mature helper T cells and immature thymocytes, as well as on monocytes and macrophages. $CD4^+$ refers to cells which stain brightly when contacted with labeled anti-CD4 antibody, and $CD4^-$ refers to cells of a type which stain the least brightly, dull or not at all, when contacted with a fluorescently labeled CD4 antibody. Generally, the cells are distinguished according to their CD4 expression levels based upon readily discernible differences in staining intensity as the CD4 staining is clearly bimodal.

As used herein, the term "CD25" refers to the alpha subunit of interleukin-2 receptor, a single-chain glycoprotein with a molecular weight of 55 kD. $CD25^{hi}$ refers to cells which stain brightly when contacted with labeled anti-CD25 antibody, $CD25^+$ refers to cells which stain less brightly when contacted with labeled anti-CD25 antibody, and $CD25^{lo/-}$ refers to cells which are of a type which stains the least brightly, dull or null when contacted with a labeled CD25 antibody. Generally, the cells are distinguished according to their CD25 expression levels based upon differences in staining intensity as is known to one of ordinary skill in the art. In some embodiments, the cut off for designating a cell as a CD25 expression category hi, +, lo, or − cell can be set in terms of the fluorescent intensity distribution observed for all the cells. Generally, cells in the top 2, 3, 4, or 5% of staining intensity are designated "hi", with those falling in the top half of the population categorized as being "+". Those cells falling below 50%, of fluorescence intensity are designated as $CD25^{lo}$ cells and below 5% as $CD25^-$ cells.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

In one aspect, the present invention relates to methods and compositions for converting non-T regulatory cells (non-Tregs) into T regulatory cells (Tregs). For example, the methods include converting $CD4^+$ or $CD4^+$ $CD25^-$ into $CD4^+$ $CD25^+$ T cells. The constitutive expression of CD25 is considered to be a characteristic feature of Tregs. Thus, Tregs are often $CD4^+$ $CD25^+$ T cells, and may be immunosuppressive. Converted $CD4^+$ $CD25^+$ T cells are referred herein as inducible Tregs (iTregs). In some instances, induction of Tregs includes both the generation of Tregs from naïve T cells and the reactivation of quiescent Tregs.

In another aspect, the present invention relates to methods for using, and compositions comprising, an iTreg cell to treat a skeletal disease or disorder, such as OI. This is because the present invention relates to the discovery that administering a composition comprising Treg in the absence of bone marrow cells is an effective therapy for enhancing bone remodeling in skeletal diseases and disorders.

The iTreg cell may be combined with at least one BM cell. In addition, conditioned media (CM), or a composition comprising at least one compound or substance secreted or released from a iTreg cell, is also useful in methods for enhancing bone remodeling, or for treating a skeletal disease or disorder, such as OI. In some instances, the composition comprising at least one compound or substance secreted or released from a iTreg cell may be combined with at least one BM cell for enhancing bone remodeling, or for treating a skeletal disease or disorder, such as OI.

In another aspect, the present invention relates to methods for using, and compositions comprising, one or more compounds to enhance bone remodeling or to treat a skeletal disease or disorder, such as OI. The one or more compounds may be administered directly to a subject in need thereof, to provide treatment of a skeletal disease or disorder, such as OI. An exemplary compound that may be used for treatment includes, but is not limited to, a PPAR-gamma agonist such as Thiazolidinedione (TZD).

Generation of iTregs and iTreg-Conditioned Medium (CM)

In one embodiment, the invention provides a composition and method for making one or more induced T regulatory cells (iTregs), which may exhibit elevated expression of FoxP3, relative to the cells before induction. In one embodiment, the invention provides a composition and method for making iTreg-conditioned medium (CM), or a composition comprising one or more iTreg-secreted compounds.

In various embodiments, the invention provides a composition and method for producing or stimulating one or more iTregs or Tregs, to enhance bone remodeling, or to treat a skeletal disease or disorder, such as OI. In one embodiment, the iTregs or Tregs are produced or stimulated in vivo. In another embodiment, the iTregs or Tregs are produced or stimulated ex vivo.

Naturally occurring T regulatory (nTreg) cells suppress immune responses and play an important role in immunotherapy against autoimmune diseases and provide transplantation tolerance. Various populations of Treg cells have been described and include naturally occurring $CD4^+$ $CD25^+$ $FoxP3^+$ cells. The natural occurring $CD4^+$ $CD25^+$ $FoxP3^+$ Treg cells represents about 5-10% of the $CD4^+$ T cells in the peripheral blood and are in a hypoproliferative state, which has hampered detailed characterization and the potential use of these cells in a therapeutic setting. In vivo uses therefore have relied on expansion protocols to generate sufficient numbers of Treg cells for in vivo use. The clinical use of Treg cells is limited by the lack of appropriate isolation and expansions protocols to generate sufficient numbers for in vivo delivery.

The present invention provides a method of generating a population of immunosuppressive Treg cells from the abundant $CD4^+$ $CD25^-$ T cell population. This method allows for the generation of Treg cells in sufficient numbers for in vivo delivery. The method can be used both for generating Treg cells for research purposes and for clinical use by infusion or transplantation in patients.

In some embodiments, the invention provides for methods of selecting or isolating the cells so identified. In some embodiments, T cells are obtained from blood (e.g., isolated from PBMC), lymphoid, thymus or any specific tissues/organ sample of interest. These tissues or organs include the pancreas, eye, heart, liver, nerves, intestine, spleen, skin, muscle, and joints.

The cells bearing the desired markers can be isolated, for instance, by the use of labeled antibodies or ligands with FACS or magnetic particles/bead technologies as known to one of ordinary skill in the art. Accordingly, in some embodiments, the invention provides a method of generating an isolated population of immunosuppressive T regulatory-cells which are substantially $CD4^+$ $CD25^+$ by obtaining a biological sample comprising non T regulatory-cells including, but not limited to, $CD4^+$, $CD4^+$ $CD25^-$, $CD4^+$ $CD25^-$ $45RA^+$ cells, and converting the non-T regulatory cells into T regulatory cells, otherwise referred to as inducible T cells (iTregs). In some embodiments, the population of converted inducible T cells is substantially $CD4^+$ $CD25^+$ T cells. In some embodiments, the population of converted inducible T cells is substantially $Foxp3^+$ T cells.

Non-Tregs, such as $CD4^+$, $CD4^+$ $CD25^-$, and $CD4^+$ $CD25^-$ $45RA^+$ cells can be isolated by negative selection (e.g., CD8 and CD25). To enhance enrichment of non-Tregs, positive selection may be combined with negative selection against cells comprising surface makers specific to non-Treg cell types, CD11b, CD16, CD19, CD36 and CD56-bearing cells. For example, a positive marker for positive selection is 45RA. As a non-limiting example, $CD4^+$ $CD25^-$ $45RA^+$ cells can initially be isolated by negative selection (e.g., CD8 and CD25). To enhance enrichment of $CD4^+$ $CD25^-$ $45RA^+$ cells, positive selection may be combined with negative selection against cells comprising surface maker 45RA.

Sources of T cells and methods of isolating particular T cell populations (e.g. $CD4^+$ cells) which can be converted by stimulation according to the methods of the present invention are well known and described in the literature. Thus for example T cells may conveniently be isolated from the blood e.g. from a peripheral blood mononuclear cell (PBMC) population isolated from blood, or from other blood-derived preparations such as leukopheresis products or from bone marrow, lymph, thymus, spleen or umbilical cord. T cell populations may be derived from any appropriate source, including human or animal sources.

The present invention also includes a combinational approach of generating T regulatory cells (Tregs) in vitro. The method includes obtaining non-Tregs (e.g., $CD4^+$ $CD25^-$ cells) or mixed populations of Tregs and non-Tregs from a subject and converting the non-Tregs into inducible Tregs. Therefore, in one embodiment, the cell population, after induction, may comprise one or more natural Tregs (nTregs) in combination with one or more iTregs.

In one embodiment, isolated $CD4^+$ spleen cells are converted to iTregs by incubating the cells in a culture medium comprising at least one selected from the group including: anti-CD3 antibody, anti-CD28 antibody, IL-2, TGF-β, and retinoic acid. In one embodiment, isolated $CD4^+$ spleen cells are converted to iTregs by incubating the cells in a culture medium comprising anti-CD3 antibody, anti-CD28 antibody, IL-2, TGF-β, and retinoic acid. In one embodiment, the isolated $CD4^+$ spleen cells are incubated for at least about 1 hour, at least about 2 hours, at least about 3 hours, at least about 4 hours, at least about 5 hours, at least about 6 hours, at least about 7 hours, at least about 8 hours, at least about 9 hours, at least about 10 hours, at least about 11 hours, at least about 12 hours, at least about 1 day, at least about 2 days, at least about 3 days, at least about 4 days, at least about 5 days, at least about 6 days, at least about 7 days, or longer, to convert the cells to iTregs.

In one embodiment, the invention provides a composition comprising one or more induced T regulatory cells (iTregs) for enhancing bone remodeling. In one embodiment, the invention provides a composition comprising one or more iTregs in combination with one or more bone marrow (BM) cells for enhancing bone remodeling. In one embodiment, the invention provides a composition comprising one or more iTregs in combination with one or more additional agents for the treatment of OI. In one embodiment, the one or more additional agents may be one or more bisphosphonates. Bisphosphonates include, but are not limited to, cholecalciferol, zoledronic acid, calcium carbonate, pamidronate, neridronate, olpadronate, alendronate, ibandronate, risedronate, zoledronate, etidronate, clodronate, and tiludronate. Other agents may include SERM such as tamoxifen, Cathepsin K inhibitors such as Odanacatib, Vitamin D analogues, RANKL monoclonal antibody such as Denosumab, recombinant growth hormone, sclerostin antibody such as Romosozumab, Blosozumab, BSP804, recombinant human PTH such as Teriparatide and TGF-β inhibitors such as SD-208, ID11, and Fresolimumab.

In one embodiment of the invention, a composition comprising one or more factors secreted or released from one or more iTregs is provided. In one embodiment, the composition comprises iTreg-conditioned medium (CM), generated by one or more iTregs. In one embodiment, the one or more iTregs are incubated for at least about 1 hour, at least about 2 hours, at least about 3 hours, at least about 4 hours, at least about 5 hours, at least about 6 hours, at least about 7 hours, at least about 8 hours, at least about 9 hours, at least about 10 hours, at least about 11 hours, at least about 12 hours, at least about 1 day, at least about 2 days, at least about 3 days, at least about 4 days, at least about 5 days, at least about 6 days, at least about 7 days, or longer, to produce iTreg-conditioned medium (CM).

In one embodiment, the invention provides a composition comprising one or more factors secreted or released from one or more iTregs for enhancing bone remodeling. In one embodiment, the composition comprising one or more factors secreted or released from one or more iTregs further comprises one or more bone marrow (BM) cells, for enhancing bone remodeling.

Therapeutic Application

The invention includes a method of suppressing an immune response in a mammal, or for enhancing bone remodeling, for the treatment of OI. The ex vivo culture-converted and culture-expanded iTregs, with or without natural Tregs, may be introduced to the host or to another patient by a number of approaches. Alternatively, iTregs and/or Tregs may be stimulated or produced in vivo. They may be injected intravenously, or transplanted. Optionally, the host may be treated with agents to promote the in vivo function and survival of the stimulated cells. Of course, the culture-expanded iTregs may also be reintroduced in a variety of pharmaceutical formulations. These may contain such normally employed additives as binders, fillers, carriers, preservatives, stabilizing agents, emulsifiers, and buffers. Suitable diluents and excipients are, for example, water, saline, and dextrose.

This method thus provides a method of achieving an osteogenic effect in a mammal, i.e. a method of promoting bone growth. In the context of treating osteogenesis imperfecta (OI), the therapeutic method enhances bone remodeling. The condition or disease typified by needing enhanced bone remodeling may be osteogenesis imperfecta (OI). Conditions in which osteogenesis would be advantageous include conditions in which a normal or an activated bone turnover is disadvantageous to the mammal. The use of such cells before, during, or after transplantation may avoid extensive bone loss which may occur in patients not being treated. The cells may be converted immediately after harvest or stored (e.g., by freezing) prior to expansion or after expansion and prior to their therapeutic use. The therapies may be conducted in conjunction with other, known bone enhancing therapies.

The methods of the present invention are particularly useful for humans, but may also be practiced on veterinary subjects. An "individual," "subject," "patient" or "host" may be referred to herein as a vertebrate, for example, a mammal. More exemplary, such individual is a human and the iTreg cells are derived from one or more humans, although animals, including animal models for human disease states, are also included in this invention and therapeutic treatments of such animals are contemplated herein. Such animal models can be used to test and adjust the compositions and methods of this invention, if desired. Certain models involve injecting animals with established cell populations. Also useful are chimeric animal models, described in U.S. Pat. Nos. 5,663,481, 5,602,305 and 5,476,993; EP application 379,554; and International Appl. WO 91/01760. Non-human mammals include, but are not limited to, veterinary or farm animals, sport animals, and pets. Accordingly, as opposed to animal models, such animals may be undergoing selected therapeutic treatments.

In one aspect, the present invention encompasses a method of reducing and/or eliminating an immune response to a transplant in a recipient by administering to the recipient of the transplant an amount of iTregs effective to reduce or inhibit host rejection of the transplant. Without wishing to be bound to any particular theory, the iTregs that are administered to the recipient of the transplant inhibit the activation and proliferation of the recipient's T cells or induce tolerance, or otherwise enhance bone remodeling.

The transplant can include a biocompatible lattice or a donor tissue, organ or cell, to be transplanted. An example of a transplant may include but is not limited to bone marrow (BM). In some instances, the transplant is a nucleic acid or a protein.

Based upon the disclosure provided herein, iTregs can be obtained from any source, for example, from the tissue donor, the transplant recipient or an otherwise unrelated source (a different individual or species altogether). The iTregs may be autologous with respect to the T cells (obtained from the same host) or allogeneic with respect to the T cells. In the case where the iTregs are allogeneic, the iTregs may be autologous with respect to the transplant to which the T cells are responding to, or the iTregs may be obtained from a mammal that is allogeneic with respect to both the source of the T cells and the source of the transplant to which the T cells are responding to. In addition, the iTregs may be xenogeneic to the T cells (obtained from an animal of a different species), for example rat iTregs may be used to suppress activation and proliferation of human T cells.

Another embodiment of the present invention encompasses the route of administering iTregs to the recipient of the transplant. iTregs can be administered by a route which is suitable for the placement of the transplant, i.e. a biocompatible lattice or a donor tissue, organ or cell, nucleic acid or protein, to be transplanted. iTregs can be administered systemically, i.e., parenterally, by intravenous injection or can be targeted to a particular tissue or organ, such as bone marrow. iTregs can be administered via a subcutaneous implantation of cells or by injection of the cells into connective tissue, for example, muscle. iTregs can also be injected intraosseously or by injection of the cells into bone.

Tregs can be suspended in an appropriate diluent, for example, at a concentration of about $5\times10^6$ cells/mL. Suitable excipients for injection solutions are those that are biologically and physiologically compatible with the Tregs and with the recipient, such as buffered saline solution or other suitable excipients. The composition for administration can be formulated, produced and stored according to standard methods complying with proper sterility and stability.

The dosage of the Tregs varies within wide limits and may be adjusted to the mammal requirements in each particular case. The number of cells used depends on the weight and condition of the recipient, the number and/or frequency of administrations, and other variables known to those of skill in the art.

Between about $10^5$ and about $10^{13}$ Tregs per 100 kg body weight can be administered to the mammal. In some embodiments, between about $1.5\times10^6$ and about $1.5\times10^{12}$ cells are administered per 100 kg body weight. In some embodiments, between about $1\times10^9$ and about $5\times10^{11}$ cells are administered per 100 kg body weight. In some embodiments, between about $4\times10^9$ and about $2\times10^{11}$ cells are administered per 100 kg body weight. In some embodiments, between about $5\times10^8$ cells and about $1\times10^{10}$ cells are administered per 100 kg body weight.

In another embodiment of the present invention, Tregs are administered to the recipient prior to, or contemporaneously with a transplant to enhance bone remodeling. While not wishing to be bound to any particular theory, Tregs can be used to condition a recipient's immune system to the transplant by administering Tregs to the recipient, prior to, or at the same time as transplantation of the transplant, in an amount effective to reduce, inhibit or eliminate an immune response against the transplant by the recipient's T cells, or to otherwise enhance bone remodeling. The Tregs may affect the T cells of the recipient such that the T cell response is reduced, inhibited or eliminated when presented with the transplant. Thus, host rejection of the transplant may be avoided, or the severity thereof reduced, by administering Tregs to the recipient, prior to, or at the same time as transplantation.

In yet another embodiment, Tregs can be administered to the recipient of the transplant after the administration of the transplant. Further, the present invention comprises a method of treating a patient who is undergoing an adverse immune response to a transplant by administering Tregs to the patient in an amount effective to reduce, inhibit or eliminate the immune response to the transplant, also known as host rejection of the transplant.

In another embodiment, iTreg conditioned media (CM), or a component thereof, is administered to a subject in a method for enhancing bone remodeling, or for treating OI, in the subject. Effective doses and concentrations of CM, or a component thereof, useful in the therapeutic methods of this invention will be apparent to the skilled artisan, who is familiar with optimizing these parameters through routine experimentation.

In another embodiment, a therapeutic method that comprises administering a composition comprising at least one iTreg cell, CM, or at least one iTreg cell and CM, further comprises one or more additional therapies for OI. In one embodiment, the one or more additional therapies for OI includes one or more additional agents.

Additional Agents

In various embodiments, the compositions and methods of the invention may further comprise one or more additional therapeutic agents for promoting bone growth and/or inhibiting bone resorption. In some embodiments, one or more of these additional agents may be combined with one or more compositions of the invention to form a combination composition. In some embodiments, one or more of these additional agents may be administered before, with, during, or after administration of one or more compositions of the invention, and may be formulated in a separate composition.

Bisphosphonates useful in the methods of the present invention can be any suitable bisphosphonate. In some embodiments, the bisphosphonates may be cholecalciferol, zoledronic acid, and/or calcium carbonate. In some embodiments, the bisphosphonates are nitrogenous, such as pamidronate (APD, Aredia), neridronate, olpadronate, alendronate (Fosamax), ibandronate (Boniva), risedronate (Actonel) and zoledronate (Zometa). In other embodiments, the bisphosphonates are non-nitrogenous, such as etidronate (Didronel), clodronate (Bonefos, Loron) and tiludronate (Skelid). One of skill in the art will appreciate that other bisphosphonates are useful in the present invention.

Selective Estrogen Receptor Modulators (SERMs) useful in the methods of the present invention can be any suitable SERM. In some embodiments, the SERM can be clomifene, raloxifene, tamoxifen, toremifene, bazedoxifene, lasofoxifene or ormeloxifene. One of skill in the art will appreciate that other SERMs are useful in the present invention.

The antiresorptive drug can also be any suitable calcitonin analog or cathepsin K inhibitor, available as miacalic, and Odanacatib. In some embodiments, calcitonin analogs useful in the methods of the present invention include, but are not limited to, miacalcic, and Odanacatib. One of skill in the art will appreciate that other calcitonin analogs are useful in the present invention.

Vitamin D analogs useful in the methods of the present invention can be any suitable Vitamin D analog. In some embodiments, Vitamin D analogs useful in the methods of the present invention include, but are not limited to, Vitamin D1 (molecular compound of ergocalciferol with lumisterol, 1:1), Vitamin D2 (ergocalciferol or calciferol), Vitamin D3 (cholecalciferol), Vitamin D4 (22-dihydroergocalciferol) and Vitamin D5 (sitocalciferol). One of skill in the art will appreciate that other Vitamin D analogs are useful in the present invention.

RankL inhibitors useful in the present invention include any compounds that inhibit the activity of RankL. For example, RankL inhibitors include, but are not limited to, the human monoclonal antibody denosumab. One of skill in the art will appreciate that other RankL inhibitors are useful in the present invention.

Other agents useful in the present invention include: any analogue of recombinant Growth hormone which has been studied in pediatric patients with OI as a potential anabolic agent and to address growth deficiency, Teriparatide (recombinant human PTH 1-34; a parathyroid hormone (PTH) analogue with bone-anabolic activity that is approved for use in adult patients with osteoporosis that stimulates both bone formation and resorption), any analogue of sclerostin inhibitory antibody, e.g., monoclonal antibodies that target sclerostin (Scl-Ab/Romosozumab; Blosozumab; BSP804) that have been developed as a novel anabolic therapy to increase bone mass (presumably, sclerostin inhibition may have a beneficial effect in disorders wherein abnormal WNT signaling plays a major role, such as WNT1-related forms of OI), and any analogue of TGF-β receptor kinase inhibitor (SD-208), TGF-β neutralizing antibody (ID11) and anti-TGF-β therapy with Fresolimumab (increased TGF-β signaling had been associated with osteopenia and bone fragility in mouse models; OI mice treated with the TGF-β inhibiting antibody ID11 showed normalized bone mass and improved bone strength).

Advantages of Using Tregs

Based upon the disclosure herein, it is envisioned that the Tregs and/or CM of the present invention can be used, optionally in conjunction with current modes, for example the use of bone marrow (BM) transplant, for the treatment of osteogenesis imperfecta (OI). A possible advantage of using Tregs and/or CM in conjunction with BM in transplantation is that by using the methods of the present invention to alter bone remodeling in a transplant recipient, the amount of immunosuppressive drug therapy used and/or the frequency of administration of immunosuppressive drug therapy can be reduced. Another advantage, as evidenced by the examples provided herein, is that administration of Tregs in combination with BM enhances bone remodeling more effectively than BM alone.

It is also contemplated that the cells and/or CM of the present invention may be administered into a recipient as a "one-time" therapy for the treatment of OI. A one-time administration of Tregs and/or CM into the recipient of the transplant may eliminate the need for chronic drug therapy. However, if desired, multiple administrations of Tregs may also be employed.

The invention described herein also encompasses a method of treating (OI) by administering Tregs and/or CM in a prophylactic or therapeutically effective amount for the treatment or amelioration of OI. Based upon the present disclosure, a therapeutic effective amount of Tregs and/or CM is an amount that inhibits or decreases the number of activated T cells, or enhances bone remodeling, when compared with the number of activated T cells, or bone remodeling, in the absence of the administration of Tregs and/or CM. In the situation of host rejection of the transplant, an effective amount of Tregs and/or CM is an amount that inhibits or decreases the number of activated T cells in the recipient of the transplant when compared with the number of activated T cells in the recipient prior to administration of the Tregs and/or CM. In the case of (OI), an effective amount of Tregs and/or CM is an amount that promotes or enhances bone generation, growth, and/or remodeling.

An effective amount of Tregs and/or CM can be determined by comparing a bone in a recipient or in a transplant prior to the administration of Tregs and/or CM thereto, with a bone in the recipient or transplant following the administration of Tregs and/or CM thereto. An increase, or the absence of a decrease, in the extent of bone remodeling in the recipient of the transplant or in the transplant itself that is associated with the administration of Tregs and/or CM thereto, indicates that the number of Tregs and/or CM administered is a therapeutic effective amount of Tregs and/or CM. Bones may be evaluated visually using standard imaging techniques as known in the art or disclosed herein, e.g., X-ray imaging, CT imaging, micro-CT imaging, and others. Bones may be evaluated functionally using standard functional, mechanical or structural tests, as known in the art.

The invention also includes methods of using Tregs and/or CM of the present invention in conjunction with one or more current modes, for example the use of OI therapy, for the treatment of OI. An advantage of using Tregs and/or CM in conjunction with standard of treatment in treatment of OI is that by using the methods of the present invention to enhance bone remodeling following transplantation, the amount of standard therapy, which may have undesired side effects, can be reduced. A benefit of reducing the use of standard OI therapy is the alleviation of unwanted side effects associated with the standard OI therapy.

It should be understood that the methods described herein may be carried out in a number of ways and with various modifications and permutations thereof that are well known in the art. It may also be appreciated that any theories set forth as to modes of action should not be construed as limiting this invention in any manner, but are presented such that the methods of the invention can be more fully understood.

In Vivo Production or Stimulation of Tregs and/or iTregs

In various embodiments, the invention provides compositions and methods for producing and/or stimulating Tregs and/or iTregs in a subject to enhance bone remodeling or to treat a skeletal disease or disorder, such as OI. In various embodiments, the compositions used to produce and/or stimulate Tregs and/or iTregs in a subject may comprise a PPAR-gamma agonist, such as Thiazolidinedione (TZD).

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore are not to be construed as limiting in any way the remainder of the disclosure.

Example 1

T Regulatory (Treg) Cell Transplantation in Osteogenesis Imperfecta (OI)

Using mice lacking functional lymphocytes, it has been demonstrated that T cells may play a role in bone regeneration with the fracture calluses of deficient mice exhibiting lower levels of bone markers leading to poor bone quality. Thus, lymphocytes exert a detrimental function during the early phase of fracture healing. A lack of T-cells delayed osteoblast maturation and prolonged the proliferative phase of fracture healing resulting in more immature osteoblasts and decreased bone formation (Toben et al, 2011, J Bone Miner Res, 26(1):113-24; Nam et al, 2012, PLoS One, 7(6):e40044). Delayed fracture healing significantly correlated with enhanced levels of terminally differentiated $CD8^+$ effector memory T cells in peripheral blood. Accordingly, depletion of $CD8^+$ T cells in a mouse osteotomy model resulted in enhanced endogenous fracture regeneration, whereas a transfer of $CD8^+$ T cells impaired the healing process (Reinke et al, 2013, Sci Transl Med, 5(177): 177ra36). Massive infiltration of T cells in the fracture callus especially near newly forming bone has been shown. Both osteoblasts and osteoclasts were found to have direct cell—cell contact with lymphocytes, strongly suggesting a regulatory role of the immune cells, specifically in the later stages of fracture healing (Konnecke et al, 2014, Bone, 64:155-65). Improved bone formation was observed after delivery of ex vivo programmed induced anti-inflammatory T regulatory cells (iTregs) cells during mesenchymal stem cell (MSC)-based bone regeneration in a calvarial defect model. The regenerated bone structure in mice infused with Treg cells was identical to no-defect control and had complete suture regeneration (Liu et al, 2011, Nat Med, 17(12): 1594-601). FOXP3-overexpressing mice, characterized by increased numbers of Tregs, have high bone volume and low osteoclast number. Thus, Treg cells can control bone resorption in vivo and can preserve bone mass during physiologic and pathological bone remodeling (Zaiss et al, 2010, Arthritis Rheum, 62(8):2328-38). Bisphosphonates, which have been widely used as a treatment for OI, have been shown to cause an elevation in the cytokine cascade of Tregs (IL-10 and TGF-β) in the peripheral blood of osteoporotic patients (Talaat et al, 2015, Inflammopharmacology, 23(2-3):119-25).

It is known that skeletal homeostasis can be dynamically influenced by the immune system. Recent studies have shown that T lymphocytes could be essential in regulating homeostasis, survival and function of not only osteoclasts but osteoblasts as well, thus playing an important role in bone turnover. Using mice lacking functional lymphocytes, it has been demonstrated that T cells play a role in bone regeneration, with fracture calluses of deficient mice exhibiting lower levels of bone markers leading to poor bone quality. A previous study also demonstrated improved bone formation after delivery of anti-inflammatory T regulatory cells (Tregs) during mesenchymal stem cell based bone regeneration. However, whether T cells, specifically Tregs, play a role in OI, a disease with high turnover and high fracture rates, has never been investigated before.

For these studies, the B6C3Fe a/a-Col1a2$^{oim}$/J (oim) model was used, which resembles Type III OI, a non-lethal but severe form. Characterization of T lymphocytes demonstrated that splenic T cells derived from oim mouse exhibited a more activated phenotype as compared to wild type (WT) T cells, which also correlated with higher secretion of effector cytokines such as IFN-γ and TNF-α. Furthermore, it was also determined that oim mouse exhibited a quantitative decrease in $CD4^+$ $CD25^+$ Foxp3$^+$ Tregs. Enhanced improvement in the trabecular and cortical parameters was observed by Micro-CT when the oim mice were transplanted with WT bone marrow (BM)+WT Tregs as compared to those transplanted with WT BM alone. It was also determined that the ability of the OI T cells to generate iTregs is the same as that of the WT. On transplanting OI mice with OI BM only and OI BM+OI iTregs, it was demonstrated that OI BM+OI iTregs transplanted OI mice had an increase in the trabecular and cortical parameters (Micro-CT) as compared to OI mice transplanted with OI BM only. To determine the mechanism of how Tregs mediate the healing of bone, their effects on osteoblasts and osteoclasts was examined. Conditioned media (CM) from ex vivo programmed iTregs from WT and OI mice not only suppressed osteoclast formation, but also caused an increase in osteoblast mineralization in oim.

It has never been investigated before whether T cells, specifically Tregs, play a role in OI, a disease with high turnover and high fracture rates. Thus, the T cell phenotype was first examined, and cytokines secreted and Treg numbers in the OI mice as compared to the wild type (WT) mice were quantified. It was then investigated whether WT and OI Treg transplantation would be beneficial in OI, leading to better bone formation.

The materials and methods of the experiments are now described.

Staining for CD44: Naïve T cells were obtained from spleens of WT and oim mouse were stained using fluorochrome conjugated CD44 antibody, acquired by FACS and analyzed by FlowJo software.

Staining for cytokines: Splenic T cells from WT and oim mice were activated for three days using anti-CD3 and anti-CD28 antibody (5 µg/ml) before being re-stimulated with similar stimuli in presence of Golgi-Plug. Intracellular staining was done with fluorochrome conjugated antibodies to IFN-γ and TNF-α and the data was acquired using FACS and analyzed by FlowJo software.

Staining for Th1, Tc1 and Th17 and Tc17 cells: Spleen-derived purified CD4$^+$ and CD8$^+$ T cells were activated for three days using anti-CD3 and anti-CD28 antibody (5 µg/ml) either under Th1, Tc1 programming conditions (i.e., IL12 (10 ng/mL), IL2 (100 U/mL), αIL4 (10 µg/mL)); or Th17, Tc17 programming conditions (i.e., IL-6 (25 ng/mL), anti-IL4 (10 µg/mL) and anti-IFN-γ (10 µg/mL), TGFβ (5 ng/mL)). On day 4 the programmed T cells were activated using PMA/ionomycin (for 6 hours) and intracellular staining for signature cytokines IFN-γ (for Th1, Tc1), and IL-17 (for Th17, Tc17) was done using fluorochrome conjugated antibodies. The samples were acquired in FACS and analyzed using FlowJo software.

Staining for Tregs: Peripheral blood or spleen-derived T cells were stained with CD4 and CD25. Intracellular staining for FoxP3 was done in a subset of these cells. The samples were acquired in FACS and analyzed using FlowJo software.

Transplantation: For these studies, B6. SJL-Ptprc$^a$ Pepc$^b$/BoyJ mice (Jackson Laboratories) as well as oim mice were used as donors for bone marrow. This is a congenic strain used in transplant studies because it carries the differential B cell antigen (CD45.1). The oim recipient mice have CD45.2 antigen, making it possible to track donor BM cells. For the generation of iTregs, the B6.Cg-Foxp$^{3tm2(EGFP)Tch}$/J mice (Jackson Labs) as well as oim mice were used. CD4$^+$ GFP$^-$ (WT) or CD4$^+$ CD25$^-$ (OI) spleen cells were sorted and cultured with anti-CD3 (5 µg/mL), anti-CD28 (5 µg/mL), IL-2 (100 U/mL), TGF-β (5 ng/mL) and retinoic acid (40 nmol/mL) for 3 days to generate iTregs, which were then analyzed for FoxP3 expression level by flow cytometry. $1 \times 10^6$ bone marrow cells (WT or OI) with and without $8.5 \times 10^5$ iTregs (WT or OI) were injected via the tail vein into sub-lethally irradiated (800 cGy) 3-month-old oim mice. Irradiated oim mouse transplanted with bone marrow from another oim mouse were used as controls. The mice were given neomycin (4 mL/bottle) in the water for 4 weeks, to prevent post-radiation infection. One month after transplant, engraftment was analyzed by percent of CD45.1 cells in peripheral blood of oim mice. Oim mice showing CD45.1 expression in the peripheral blood were designated as engrafted mice. Three-four months after transplantation, tibia from the control OI-OI, bone marrow only and bone marrow+iTreg transplanted were analyzed by using Siemens Inveon Micro-CT scanner as well as high-resolution Scanco µCT40 scanner (Scanco).

Micro-CT: For Siemens Inveon Micro-CT scanner, high-resolution (15-30 micrometer) micro-CT images were obtained in live mice under isoflurane anesthesia. Biomedical image analysis software (CT Bone Visualization and Analysis) was used to generate ROI area measurements and tissue mineral density plots. For very high resolution micro-CT scanning, dissected tibia, after euthanasia, was scanned by a cone beam micro-CT system µCT40 (Scanco). Scans were evaluated using µCT Evaluation Program V6.5 (Scanco). Cortical sample ROIs were contoured on exterior perimeter of each slice. Trabecular scans were contoured about the inner cortical perimeter, representing a 2.33 mm region located 180 µm distal to growth plate. Segmentation values were set to distinguish bone from non-mineralized tissue within respective ROI.

Generation of CM: Spleen cells were isolated from 6-10 weeks old WT and oim mice. Mice less than 12 weeks of age and both genders were used. CD4$^+$ CD25$^-$ cells were sorted and cultured with anti-CD3 (5 µg/mL), anti-CD28 (5 µg/mL), IL-2 (100 U/mL), TGF-β (5 ng/mL) and retinoic acid (40 nmol/mL) for 3 days to generate iTregs. At this point, a cohort of cells was analyzed for FoxP3 expression to confirm generation of Tregs. The cells were then washed and cultured in media only for an additional 24 hours and this media after 24 hours was collected as Treg conditioned media (CM). The CM was centrifuged, supernatant collected and stored at −80° C. until use.

Culture of Osteoblasts: For these studies, bone marrow was harvested from calvaria of 4-5 week oim mice. Mice of both genders were used. $1-2 \times 10^6$ cells were plated per well and cultured in osteogenic media consisting of α-MEM/15% FBS including ascorbic acid 2-phosphate (Wako) and β-glycerophosphate (Sigma). Fresh CM was added at each media change which was twice per week. At the end of culture, cells were stained for Alizarin Red (IHC World) to assess functionality of osteoblasts in depositing mineral.

Culture of osteoclasts: Bone marrow was harvested from tibia and femur of 4-5 week old oim mice. Mice of both genders were used. Cells were cultured into a 100 mm dish in α-MEM/10% FBS overnight, supernatant collected next day and centrifuged to collect non-adherent cells. These were then plated at $10 \times 10^6$ cells per well in the same media as above, supplemented with RANKL and M-CSF (osteoclastic media). As with osteoblast experiments, fresh CM was added at each media change which is twice per week. Osteoclast differentiation after 5-7 days of culture was evaluated by staining for TRAP using leukocyte acid phosphatase kit (Sigma) to assess for formation of multinucleated TRAP$^+$ osteoclasts.

The results of the experiments are now described.

Induced T Regulatory Cells (iTregs) Enhance Bone Remodeling in vivo

Osteogenesis Imperfecta (OI) is a brittle bone disease, with an incidence of 1 in 15-20,000 live births. OI is also referred to as a "Collagen-related disorder" as OI can be caused by mutations in Type I collagen (Classical OI; autosomal dominant) as well as mutations in non-collagenous genes whose protein products interact with collagen (Non-classical; Autosomal recessive). There is presently no cure for OI, only symptomatic treatment (FIG. 1).

Figure 2:
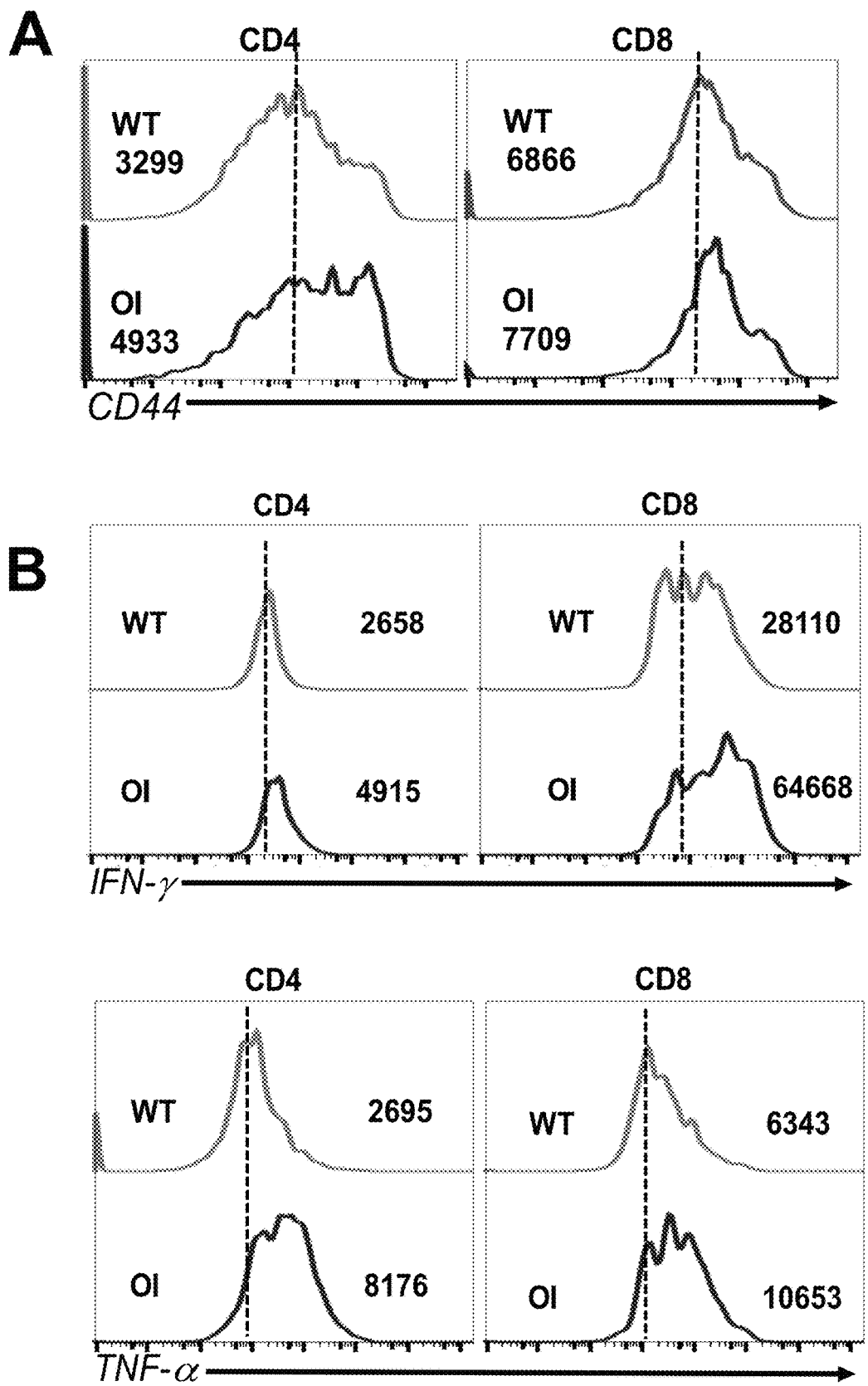
FIG. 2, comprising

The oim/oim model (B6C3Fe a/a-Col1a2$^{oim}$m/J) was used for experiments. This model resembles a severe non-lethal form of human OI. The oim mutation arose spontaneously in 1985 and it has since been determined that the underlying defect in the oim mouse is a mutation in COL1A2. This mutation changes the reading frame at the 3' end of the mRNA causing synthesis of an altered C-propeptide that ultimately inhibits the association of these molecules into heterotrimeric type I procollagen bundles in the bone matrix. Instead homotrimers are formed which interferes with the integrity and quantity of the osteoid that accumulates in the bone. This mouse model has been shown to have a phenotype similar to that seen in human type III OI, including a decreased body size, abnormal bone mineralization (contributing to the brittleness of the bones), decreased bone density and a fragile skeleton susceptible to fractures. While the skeleton becomes progressively deformed with age, homozygous mice can live a normal life span. The heterozygous mice simulate the mild form of the disease in which the bones show abnormal cortical morphology and reduced bone mechanical strength even though no fractures are seen. The oim model mice had an activated phenotype and enhanced cytokine secretion by T cells. (FIG. 2) Spleen derived naïve T cells from WT and oim mice were stained using fluorochrome conjugated antibody for various cell surface molecules, and analysis was performed after acquiring the samples in FACS and analyzed. Naïve splenic T cells obtained from OI mice exhibited relatively higher expression of activation molecule CD44, indicating their activated phenotype. (FIG. 2A) Splenic T cells from WT and oim mice were activated for three days using anti-CD3 and anti-CD28 antibody (5 µg/mL) before being re-stimulated with similar stimuli in presence of Golgi-Plug. Intracellular staining was performed with fluorochrome conjugated anti-cytokine antibody, and data was acquired using FACS. FIG. 2B upper panel represents IFN-γ and lower panel is from TNF-α secretion. The numerical values within each display are mean fluorescence intensity (MFI). The dotted vertical line indicates the mean position of the peak in WT T cells to visually compare the relative expression between samples. There is a greater expression of both IFN-γ and TNF-α in OI T cells as compared to WT T cells.

Figure 3:
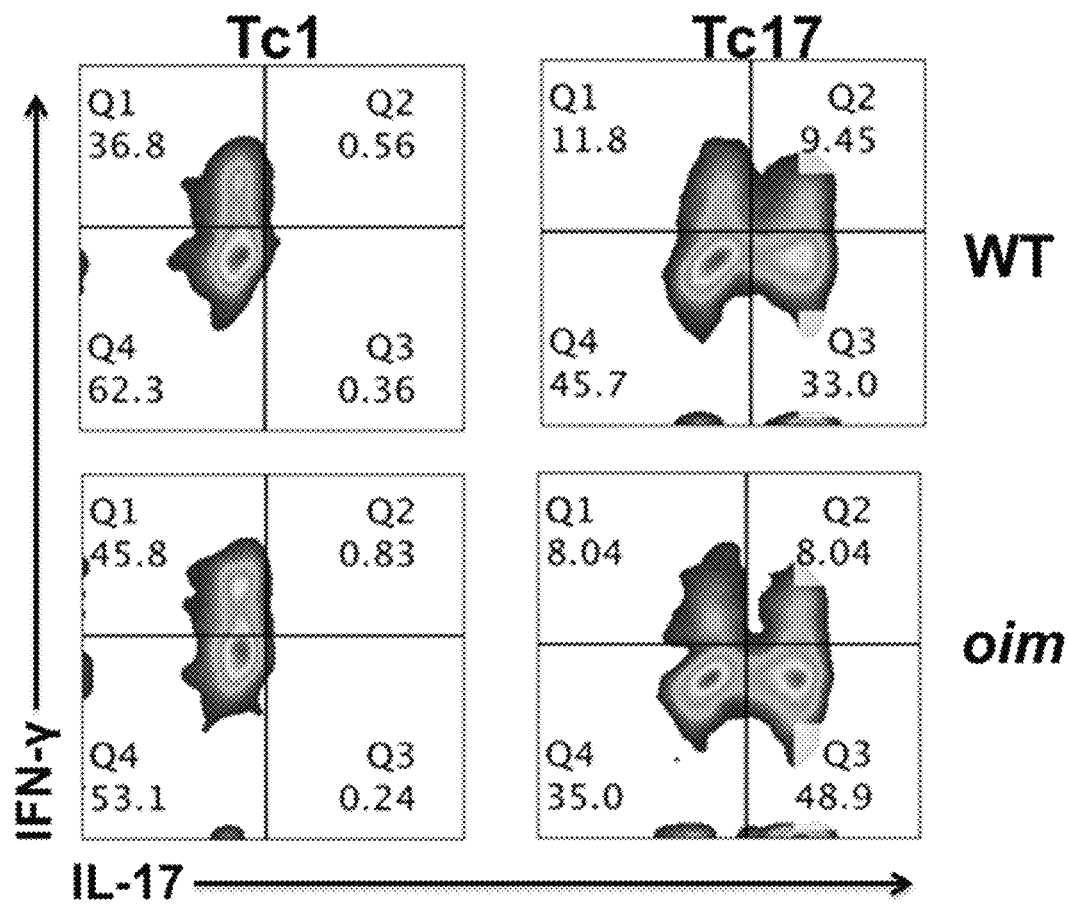
FIG. 3 depicts results from example experiments, demonstrating the increased percent of Tc1 and Tc17 cells by oim T cells upon ex vivo programming. Ex vivo programming of spleen derived purified $CD4^+$ and $CD8^+$ T cells were activated for three days using anti-CD3 (5 μg/mL) and anti-CD28 antibody (5 μg/mL) either under Th1, Tc1 programming conditions (i.e. IL-12 (10 ng/mL), IL-2 (100 U/mL), αIL-4 (10 μg/mL)); or Th17, Tc17 programming conditions (i,e. IL-6 (25 ng/mL), anti-IL4 (10 μg/mL) and anti-IFN-γ (10 μg/mL), TGF-β (5 ng/mL)). On day 4, the programmed T cells were activated using PMA/ionomycin (for 6 hours) and intracellular staining for signature cytokines IFN-γ (for Th1, Tc1), and IL-17 (for Th17, Tc17) was done using fluorochrome conjugated antibody. The samples were acquired with FACS and analyzed using FlowJo software. Data from one of three experiments with similar results is shown. It was observed that the percent of cells secreting IFN-γ were more in Tc1 from OI mouse derived T cells as compared to T cell derived from WT mouse. Similarly, percent of cells secreting IL17 were more in Tc17 obtained from OI mice.
Figure 4:
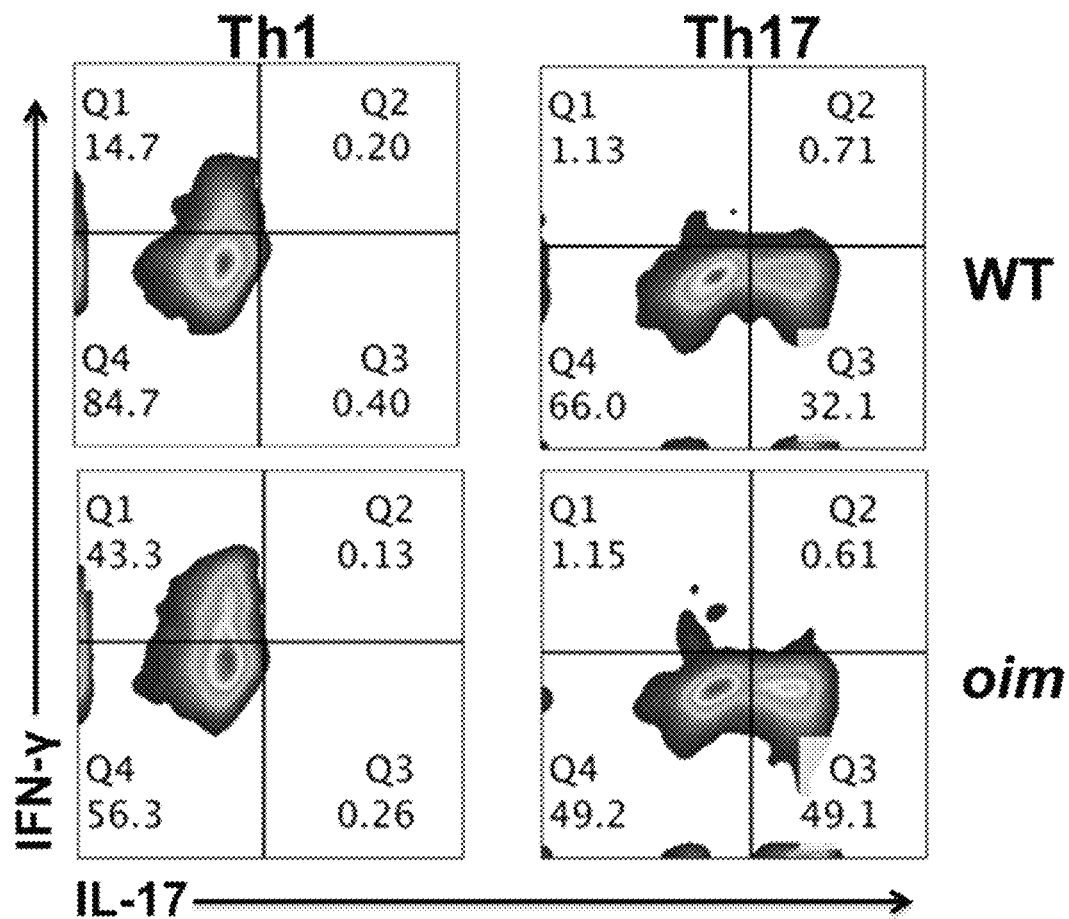
FIG. 4 depicts results from example experiments, demonstrating the increased percent of Th1 and Th17 cells by oim T cells upon ex vivo programming. Ex vivo programming of spleen derived purified $CD4^+$ and $CD8^+$ T cells were activated for three days using anti-CD3 (5 μg/mL) and anti-CD28 antibody (5 μg/mL) either under Th1, Tc1 programming conditions (i.e. IL-12 (10 ng/mL), IL-2 (100 U/mL), αIL-4 (10 μg/mL)); or Th17, Tc17 programming conditions (i,e. IL-6 (25 ng/mL), anti-IL4 (10 μg/mL) and anti-IFN-γ (10 μg/mL), TGF-β (5 ng/mL). On day 4, the programmed T cells were activated using PMA/ionomycin (for 6 hours) and intracellular staining for signature cytokines IFN-γ (for Th1, Tc1), and IL-17 (for Th17, Tc17) was done using fluorochrome conjugated antibody. The samples were acquired with FACS and analyzed using FlowJo software. Data from one of three experiments with similar results is shown. It was observed that the percent of cells secreting IFN-γ were more in Th1 from OI mouse derived T cells as compared to T cell derived from WT mouse. Similarly, percent of cells secreting IL17 were more in Th17 obtained from OI mice.

There was an increased percent of Tc1 and Tc17 cells (FIG. 3) and Th1 and Th17 cells (FIG. 4) upon ex vivo programming. Ex vivo programming of spleen derived purified $CD4^+$ and $CD8^+$ T cells were activated for three days using anti-CD3 and anti-CD28 antibody (5 µg/mL) either under Th1, Tc1 programming conditions (i.e. IL-12 (10 ng/mL), IL-2 (100 U/mL), αIL-4 (10 µg/mL)); or Th17, Tc17 programming conditions (i,e., IL-6 (25 ng/mL), anti-IL4 (10 µg/mL) and anti-IFN-γ (10 µg/mL), TGF-β (5 ng/mL)). On day 4, the programmed T cells were activated using PMA/ionomycin (for 6 hours) and intracellular staining for signature cytokines IFN-γ (for Th1, Tc1), and IL-17 (for Th17, Tc17) was done using fluorochrome conjugated antibody. The samples were acquired with FACS and analyzed using FlowJo software. Data from one of three experiments with similar results is shown. It was observed that the percent of cells secreting IFN-γ were more in Th1 or Tc1 from OI mouse derived T cells as compared to T cell derived from WT mouse. Similarly, percent of cells secreting IL17 were more in Th17 or Tc17 obtained from OI mice (FIG. 3, FIG. 4).

Figure 5:
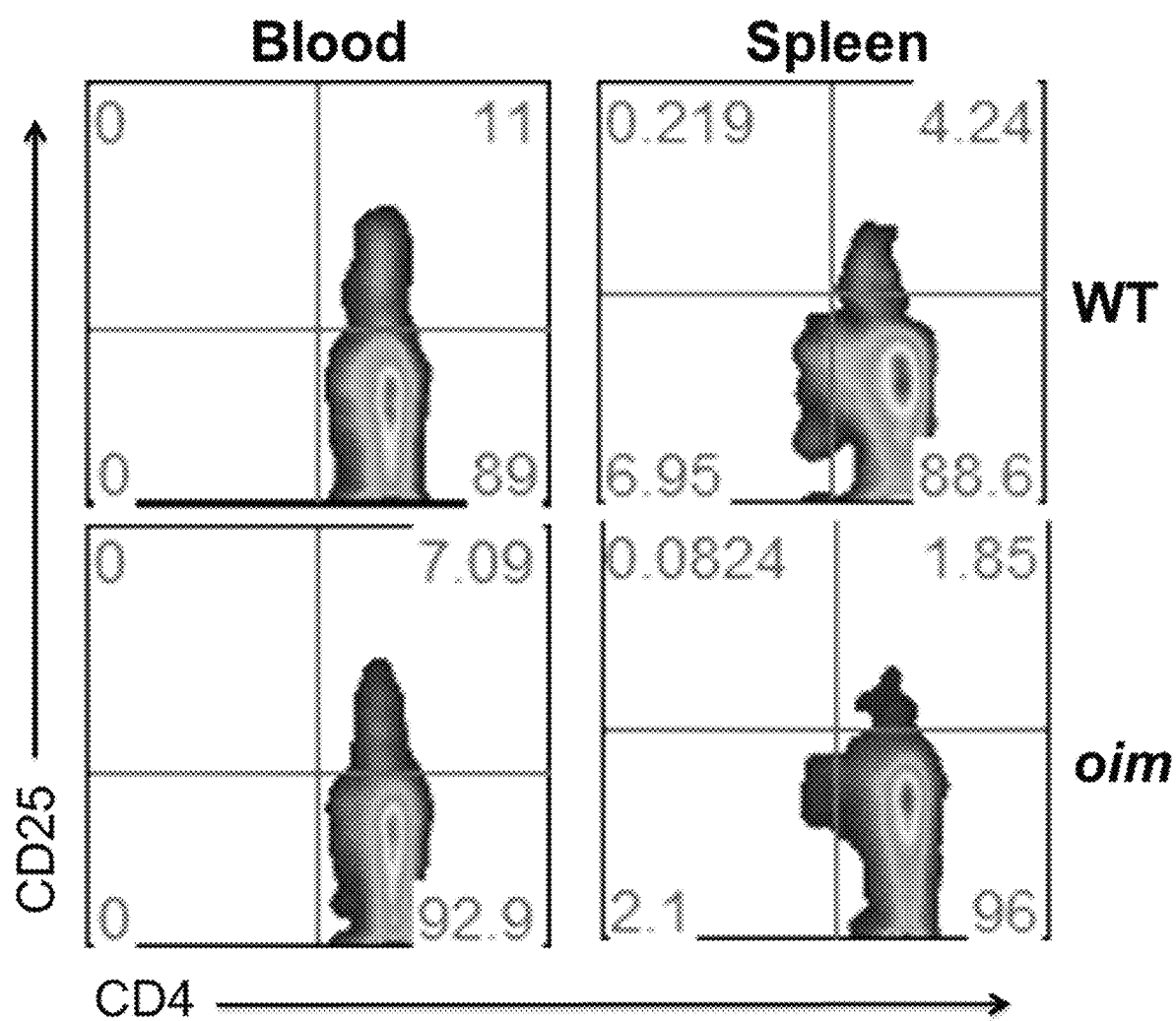
FIG. 5 depicts results from example experiments, demonstrating the reduced number of $CD4^+$ $CD25^+$ cells in oim mice. Given the enhanced effector phenotype by OI mice derived naïve T cells, it was desired to determine the cause of the higher activated phenotype in naïve T cells. Peripheral blood (left column) and spleen derived T cells (right column) were stained using fluorochrome conjugated CD4 and CD25 antibody to compare their percentages between the WT (upper row) and oim (lower row) mice. Data from one of three experiments with similar results is shown. As compared to WT counterpart, OI mice have 40-60% reduction in $CD4^+$ $CD25^+$ cells.

There was a reduced number of $CD4^+$ $CD25^+$ cells in oim mice. Given the enhanced effector phenotype by OI mice derived naïve T cells, it was desired to determine the cause of the higher activated phenotype in naïve T cells. Peripheral blood (FIG. 5, left column) and spleen derived T cells (FIG. 5, right column) were stained using fluorochrome conjugated CD4 and CD25 antibody to compare their percentages between the WT (upper row) and oim (lower row) mice. Data from one of three experiments with similar result is shown. As compared to WT counterpart, OI mice have 40-60% reduction in $CD4^+$ $CD25^+$ cells (FIG. 5).

Figure 6:
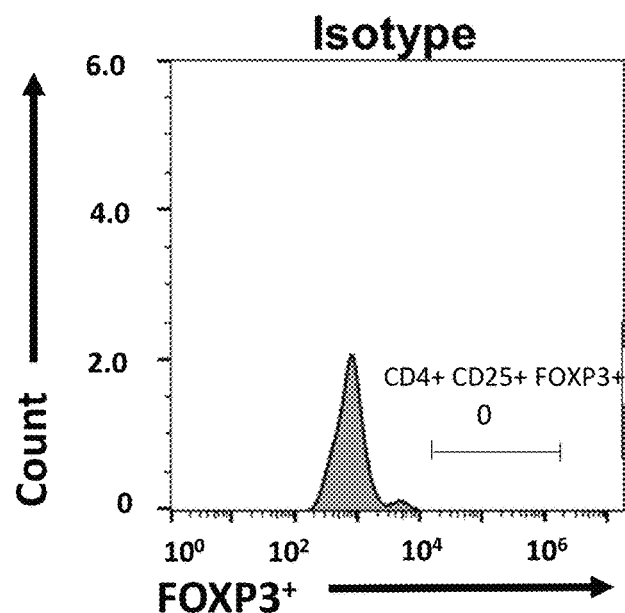
FIG. 6 depicts results from example experiments, demonstrating the reduced number of natural T Regulatory Cells (nTregs) in oim mice. In order to confirm that the low $CD4^+$ $CD25^+$ population seen in oim mice is the natural T regulatory cells (nTregs), the $CD4^+$ $CD25^+$ cells were stained with FoxP3, which is the master regulator in the development and functions of Tregs. WT and oim mouse derived splenic T cells were stained with fluorochrome conjugated antibodies against CD4, CD25 and FoxP3 and the percentage of $CD4^+$ $CD25^+$ $FoxP3^+$ cells was analyzed. Data was acquired using FACS and analyzed using FlowJo software. Data from one of two experiments with similar results is shown. It was observed that the nTreg numbers tracked by $CD4^+$ $CD25^+$ $FoxP3^+$ using flow cytometry was decreased by about 55-61% in the oim mice compared to the WT control mice.
Figure 6:
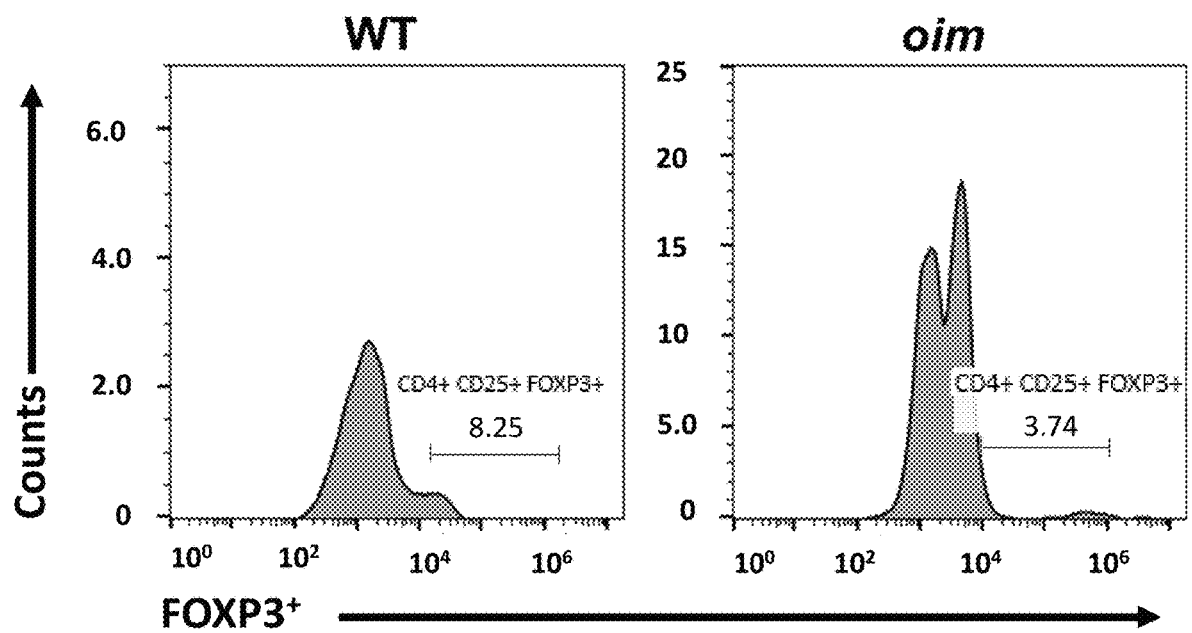

There was a reduced number of natural T Regulatory Cells (nTregs) in oim mice. In order to confirm that the low $CD4^+$ $CD25^+$ population seen in oim mice is the natural T regulatory cells (nTregs), the $CD4^+$ $CD25^+$ cells were stained with FOXP3, which is the master regulator in the development and functions of Tregs. WT and oim mouse derived splenic T cells were stained with fluorochrome conjugated antibodies against CD4, CD25 and FoxP3 and the percentage of $CD4^+$ $CD25^+$ $FOXP3^+$ cells was analyzed. Data was acquired using FACS. It was observed that the nTreg numbers tracked by $CD4^+$ $CD25^+$ $FoxP3^+$ using flow cytometry was decreased by about 55-61% in the oim mice compared to the WT control mice (FIG. 6).

Figure 7:
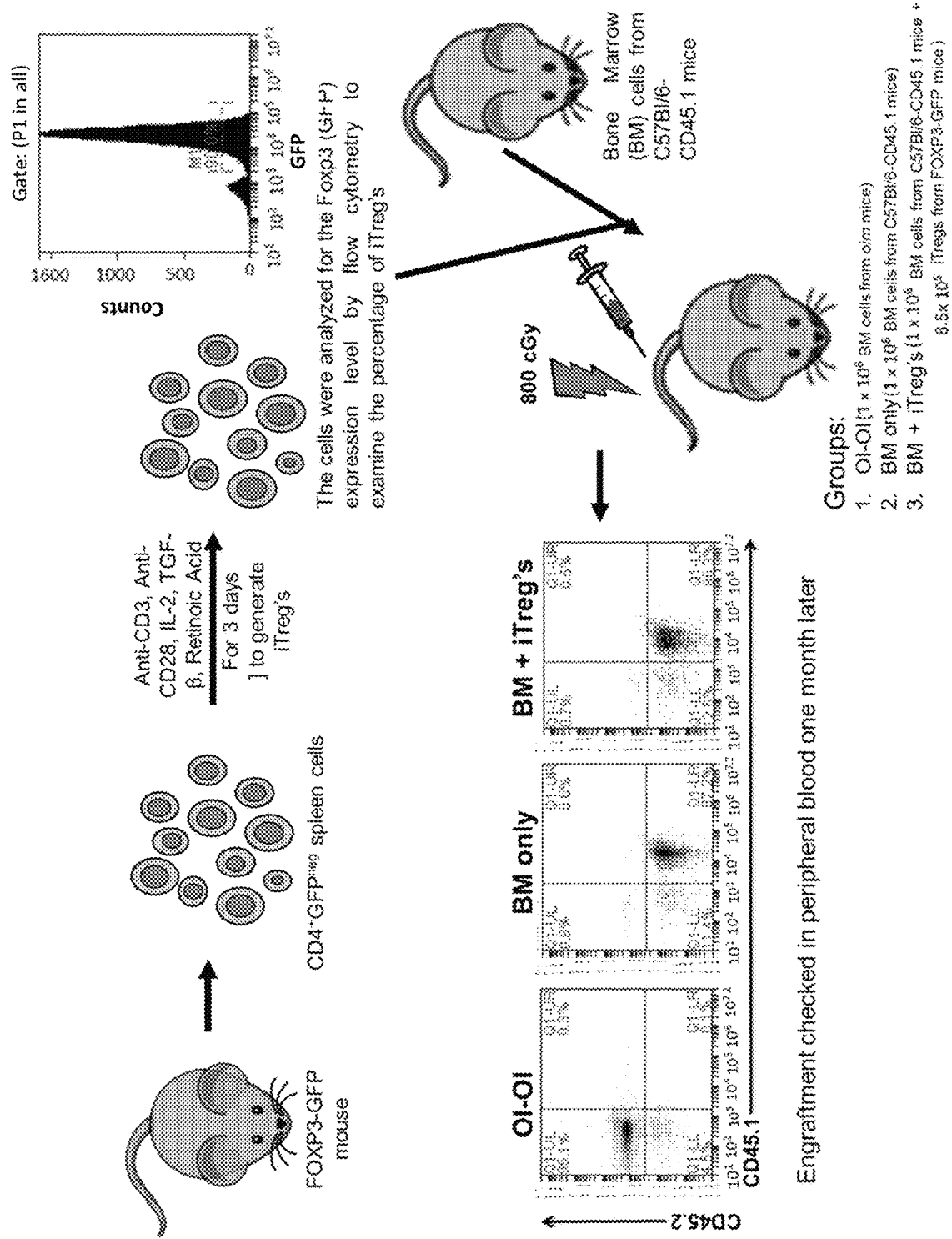
FIG. 7 depicts an illustration of the procedure for induced T regulatory Cell (iTreg) Transplantation in oim mice. Recipients included the oim/oim model (B6C3Fe a/a-Col1a2$^{oim}$/J), which resembles the type III severe, but non-lethal form of human OI. Recipients were deficient in Col1A2, therefore had triple helix made by Col1A1 only. Recipients had decreased body size, abnormal bone mineralization, decreased bone density and fractures. The recipient homozygous oim mice live a normal life span. OI mice have CD45.2 antigen, making it possible to track donor BM cells. Donor material included bone marrow cells from B6.SJL-Ptprca Pepcb/BoyJ mice (C57Bl/6-CD45.1; congenic strain used in transplant studies, because it carries the differential B cell antigen) as well as iTregs from B6.Cg-FOXP3tm2(EGFP)Tch/J mice (FoxP3-GFP mice). iTregs were obtained by culturing the $CD4^+$ $GFP^-$ spleen cells in a cocktail of anti-CD3 (5 µg/mL), anti-CD28 (5 µg/mL), IL-2 (100 U/mL, TGF-β (5 ng/mL) and retinoic acid (40 nmol/mL) for 3 days. After 3 days, the cells were analyzed for GFP expression to confirm the presence and the percentage of iTregs. Cells were transplanted into sub-lethally irradiated (800cGy) oim mice and engraftment confirmed one month after transplantation by examing the presence of CD45.1 cells in the peripheral blood of oim mice.

Induced T regulatory Cell (iTreg) Transplantation is an effective therapy in oim mice. Recipients included the oim/oim model (B6C3Fe a/a-Col1a2$^{oim}$/J), which resembles the type III severe, but nonlethal form of human OI. Recipients were deficient in Col1A2, therefore had lowered triple helix made by Col1A1. Recipients had decreased body size, abnormal bone mineralization, decreased bone density, and fractures. The recipient homozygous oim mice live a normal life span. OI mice have CD45.2 antigen, making it possible to track donor BM cells. Donor material included bone marrow cells from B6.SJL-Ptprca Pepcb/BoyJ mice (C57B1/6-CD45.1; congenic strain used in transplant studies, because it carries the differential B cell antigen) iTregs from B6.Cg-FOXP3tm2(EGFP)Tch/J mice (FOXP3-GFP mice) (FIG. 7).

Figure 8:
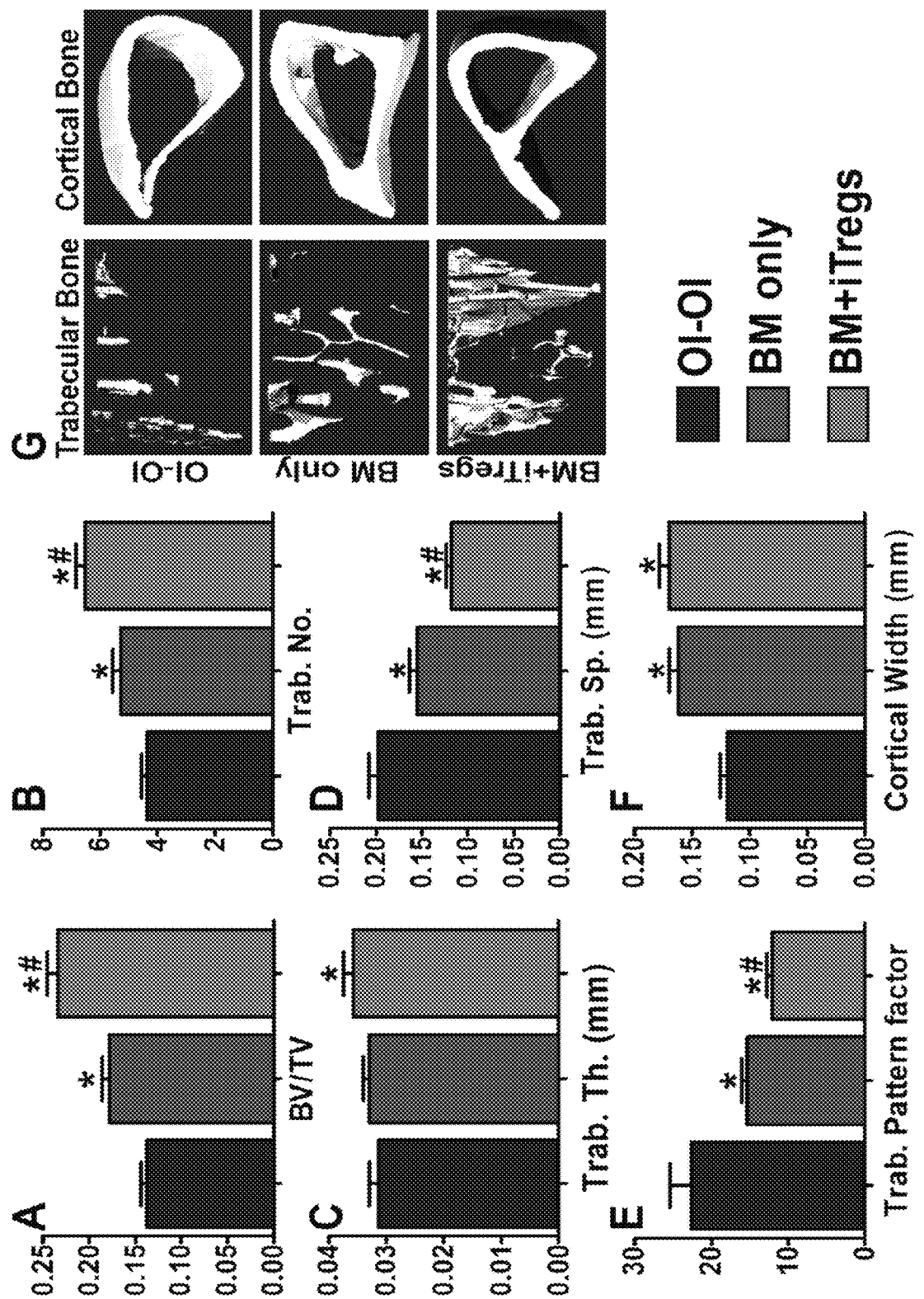
FIG. 8, comprising
Figure 8H:
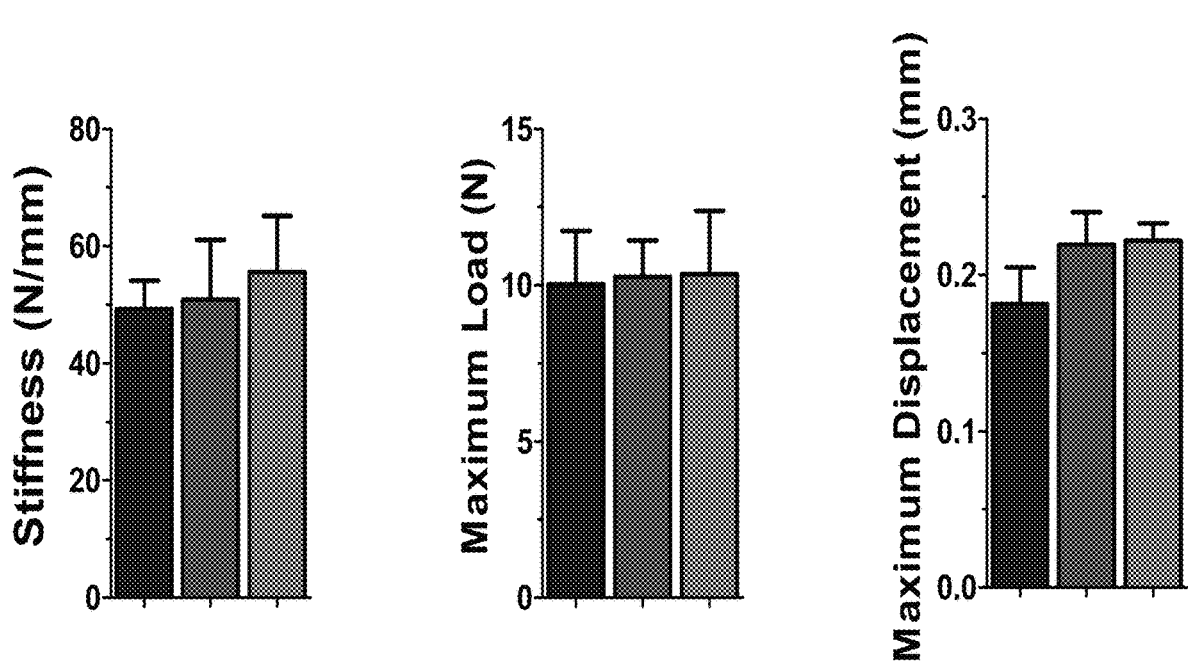

The morphometric properties of tibia from OI-OI, oim transplanted with BM only and oim transplanted with BM+iTregs were compared (FIG. 8). To determine in vivo functionality of iTregs, oim mice were transplanted with total BM cells with and without iTregs and the changes in bone morphology tracked by Micro-CT 3-4 months after transplantation. The increase in bone volume/total volume and trabecular number observed in oim mice transplanted with WT BM+iTregs was significantly greater than increase observed with BM transplantation only. A concomitant significantly greater decrease in trabecular spacing was also observed. Trabecular pattern factor showed a concomitant significant decrease. There was a significant increase in trabecular thickness in the BM+iTreg transplanted group only. Cortical width also showed a significant increase after BM and BM+iTreg transplantation. This can also be appreciated in the representative images of the trabecular bone (left panel) and the cortical bone (right panel). (*$p<0.05$ BM or BM+iTreg versus OI-OI; #$p<0.05$ BM+iTreg versus BM only). (FIG. 8).

Figure 9:
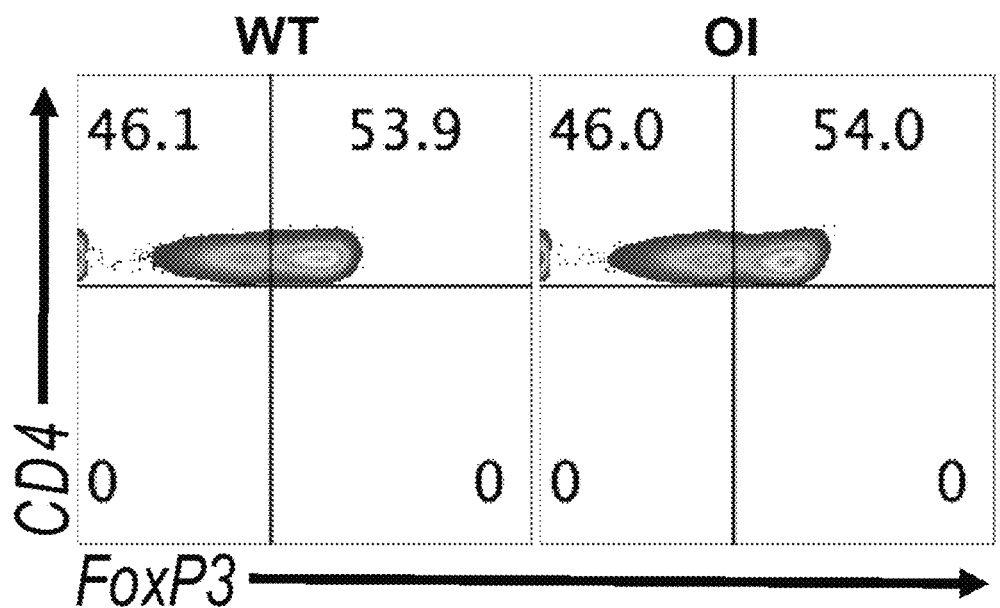
FIG. 9 depicts results from example experiments, demonstrating that OI mice have the same ability to form iTregs as WT mice. This is important to know in order to proceed with the hypothesis that auto-transplantation of iTregs would have the same beneficial effects. WT and oim mouse derived splenic $CD4^+$ $CD25^-$ T cells were programmed ex vivo using anti-CD3 (5 µg/mL) and anti-CD28 (5 µg/mL) in presence of recombinant TGF-β (5 ng/mL) and IL-2 (100 U/mL) for three days. The iTregs were characterized by staining for fluorochrome conjugated antibodies against CD4 and FoxP3. Data was acquired using FACS and analyzed using FlowJo software. OI mice have the same ability to form iTregs as WT mice.
Figure 10:
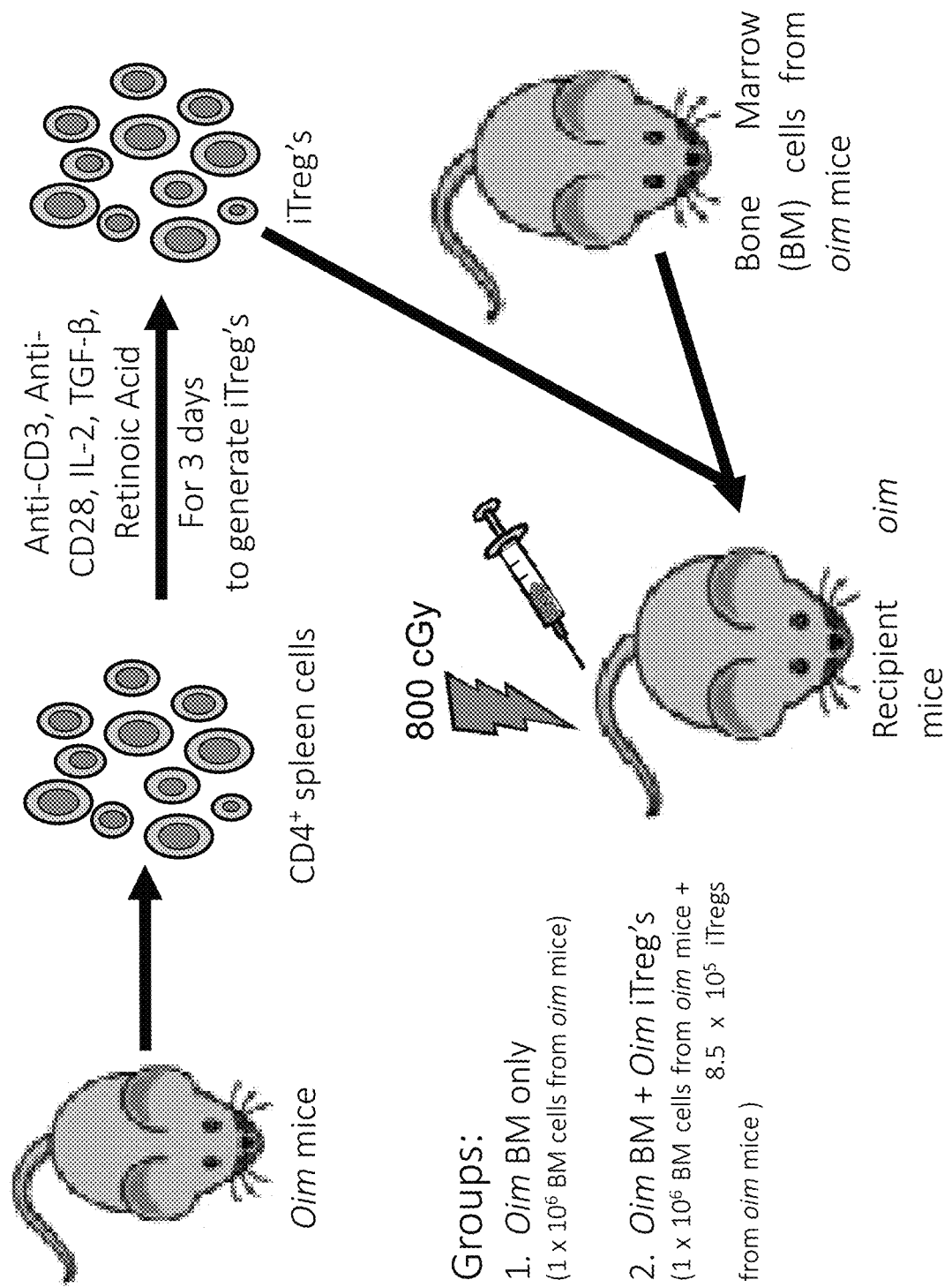
FIG. 10 depicts an illustration of the procedure for OI induced T regulatory Cell (iTreg) Transplantation in oim mice. Recipients and donors included the oim/oim model (B6C3Fe a/a-Col 1a2$^{oim}$/J), which resembles the type III severe, but nonlethal form of human OI. iTregs were obtained by culturing the $CD4^+$ spleen cells from OI mice in a cocktail of anti-CD3 (5 µg/mL), anti-CD28 (5 µg/mL), IL-2 (100 U/mL, TGF-β (5 ng/mL) and retinoic acid (40 nmol/mL) for 3 days. After 3 days, the cells were analyzed for FoxP3 expression to confirm the presence and the percentage of iTregs. BM was also obtained from another OI mouse. Cells were transplanted into sub-lethally irradiated (800 cGy) oim mice.

OI mice have the same ability to form iTregs as WT mice. This is important to know in order to proceed with the hypothesis that auto-transplantation of iTregs would have the same beneficial effects. WT and oim mouse derived splenic $CD4^+$ $CD25^-$ T cells were programmed ex vivo using anti-CD3 (5 µg/mL) and anti-CD28 (5 µg/mL) in presence of recombinant TGF-β (5 ng/mL) and IL-2 (100 U/mL) for three days. The iTregs were characterized by staining for fluorochrome conjugated antibodies against CD4 and FoxP3. Data was acquired using FACS and analyzed using FlowJo software. OI mice have the same ability to form iTregs as WT mice (FIG. 9).

Figure 11:
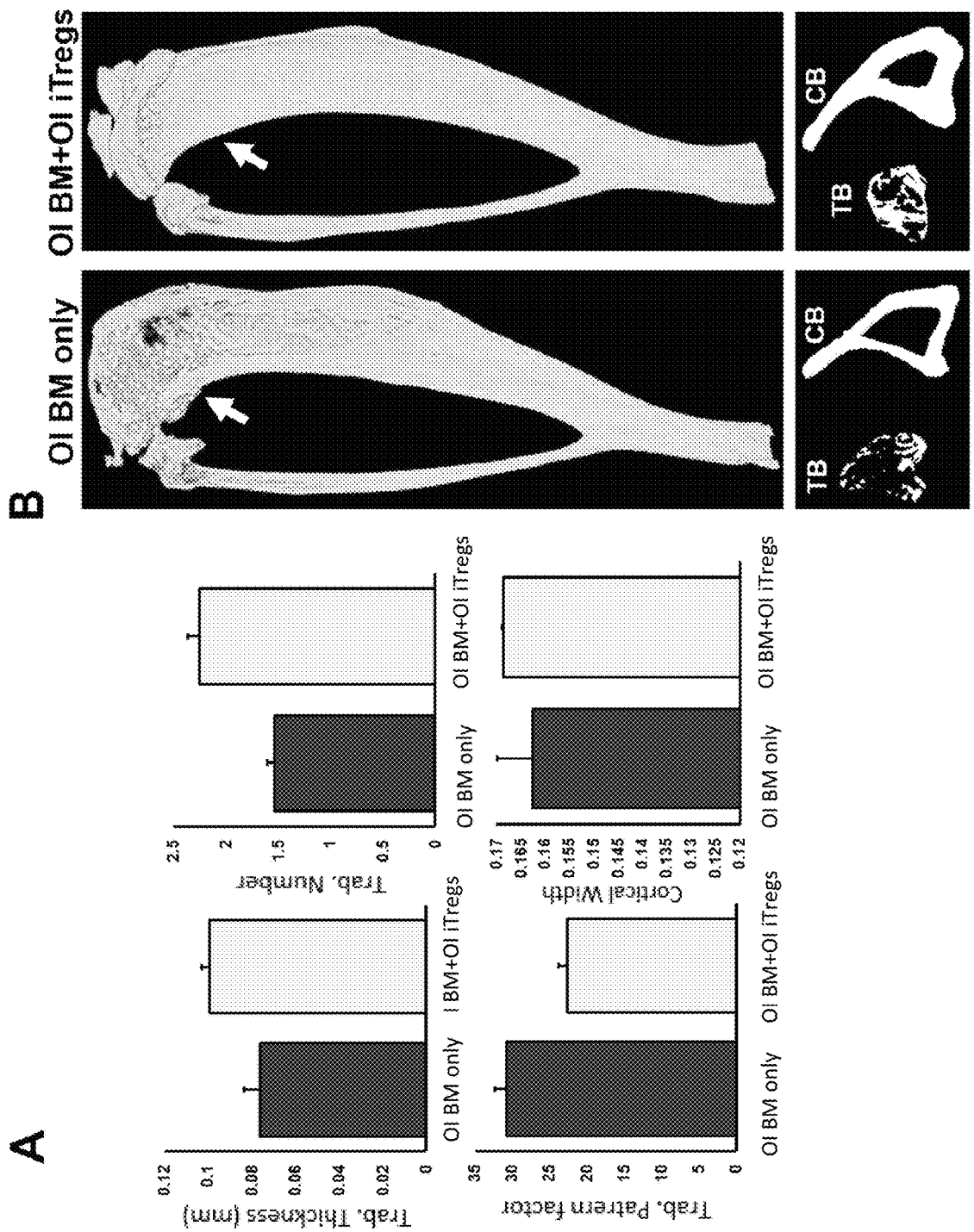
FIG. 11, comprising
Figure 11C:
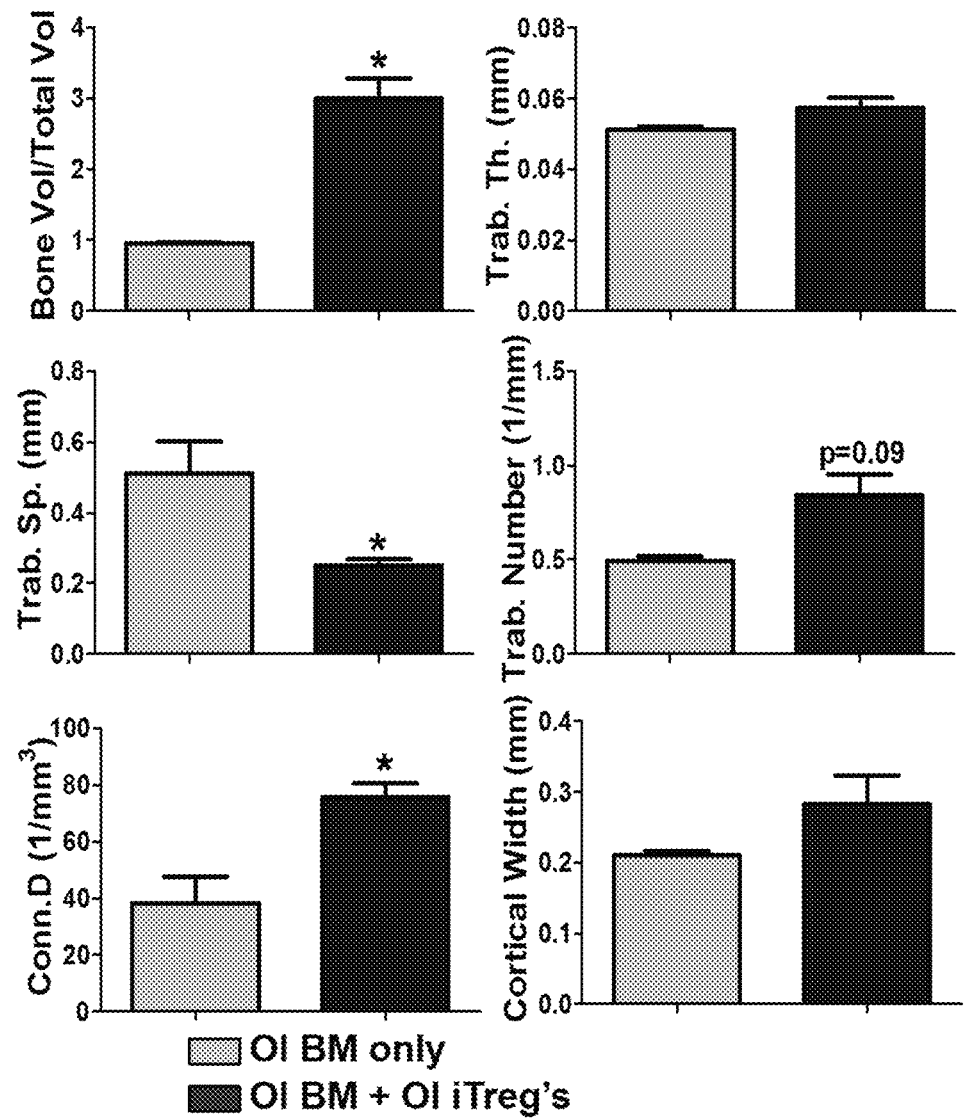
FIG. 11C shows there was a significant increase in BV/TV and Conn. Density, while a trend for increase can be seen in trabecular thickness, trabecular number and cortical width. There was a significant decrease in trabecular spacing. This can also be observed in representative images of the trabecular bone (left panel) and the cortical bone (right panel) (FIG. 11D). Markedly improved trabecular architecture is seen in oim mouse transplanted with oim BM+oim iTregs as compared to oim BM only; *p<0.05.
Figure 11D:
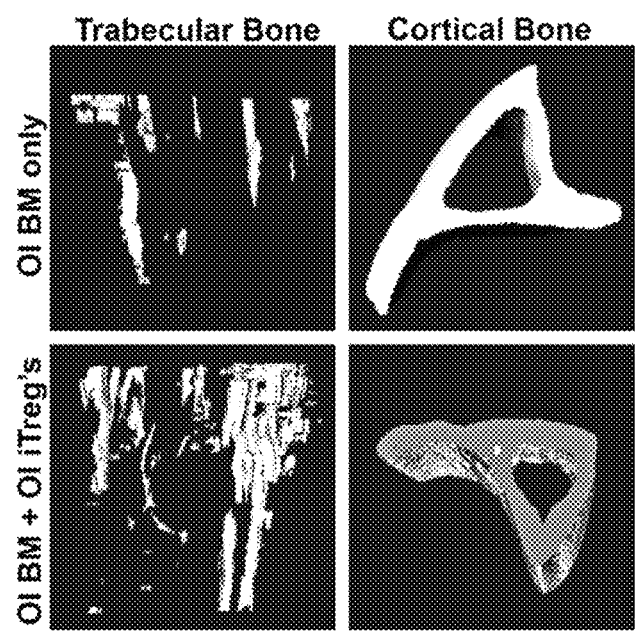
FIG. 11A and FIG. 11E, depicts results from example experiments, demonstrating the morphometric comparison of tibia from oim mice transplanted with BM only from another oim mice (OI BM only) and tibia from oim mice transplanted with BM from another oim mice along with iTregs from another oim mice (OI BM+OI iTregs). To determine if auto-transplantation would be beneficial in the treatment of OI, oim mice were transplanted with total BM cells from another OI mice with and without iTregs from another OI mice and the changes in bone morphology were tracked by Micro-CT 3 months after transplantation. There was a trend for increase in the trabecular thickness, trabecular number and cortical width (FIG. 11A). Trabecular pattern factor also showed a greater decrease, indicating improvement in connectivity and structure of trabeculae (FIG. 11A). This can also be appreciated in the representative images of the whole tibia (upper panel) and the cross section of the trabecular bone (TB) and cortical bone (CB) (lower panel) (FIG. 11B). Markedly improved architectural structure of the tibia (pointed by arrows in upper panel) as well as of the TB and CB is seen in OI mouse transplanted with OI BM+OI iTregs as compared to OI BM only.
Figure 11E:
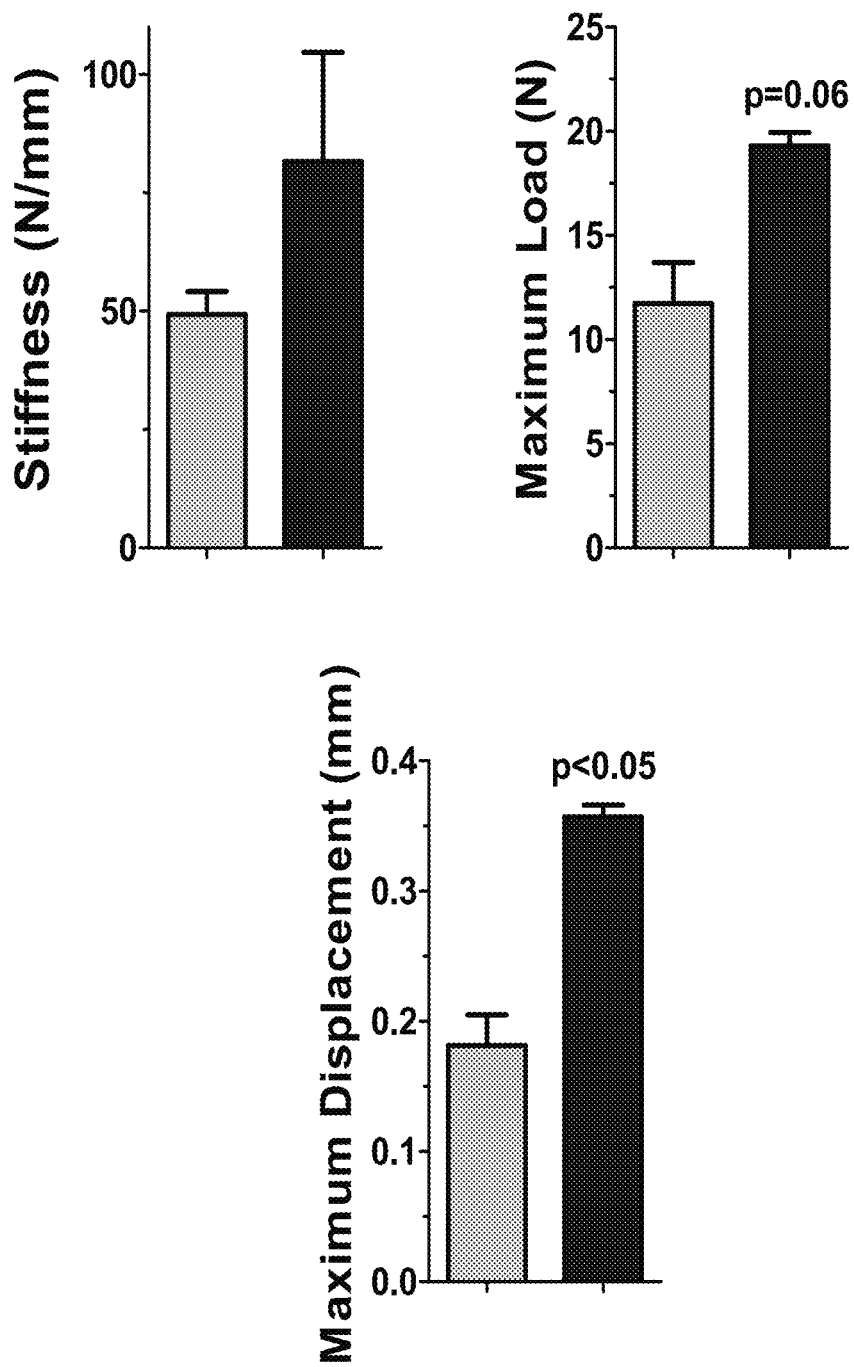

Morphometric comparison of tibia from oim mice transplanted with BM only from another oim mice (OI BM only) and tibia from oim mice transplanted with BM from another oim mice along with iTregs from another oim mice (OI BM+OI iTregs) was conducted. To determine if auto-transplantation would be beneficial in the treatment of OI, oim mice were transplanted with total BM cells from another OI mice with and without iTregs from another OI mice and the changes in bone morphology tracked by Micro-CT 3 months after transplantation. There was a trend for increase in the trabecular thickness, trabecular number and cortical width. Trabecular pattern factor also showed a greater decrease, indicating improvement in connectivity and structure of trabeculae. This can also be appreciated in the representative images of the whole tibia (upper panel) and the cross section of the trabecular bone (TB) and cortical bone (CB) (lower panel). Markedly improved architectural structure of the tibia (pointed by arrows in upper panel) as well as of the TB and CB is seen in OI mouse transplanted with OI BM+OI iTregs as compared to OI BM only (FIG. 11).

Figure 12:
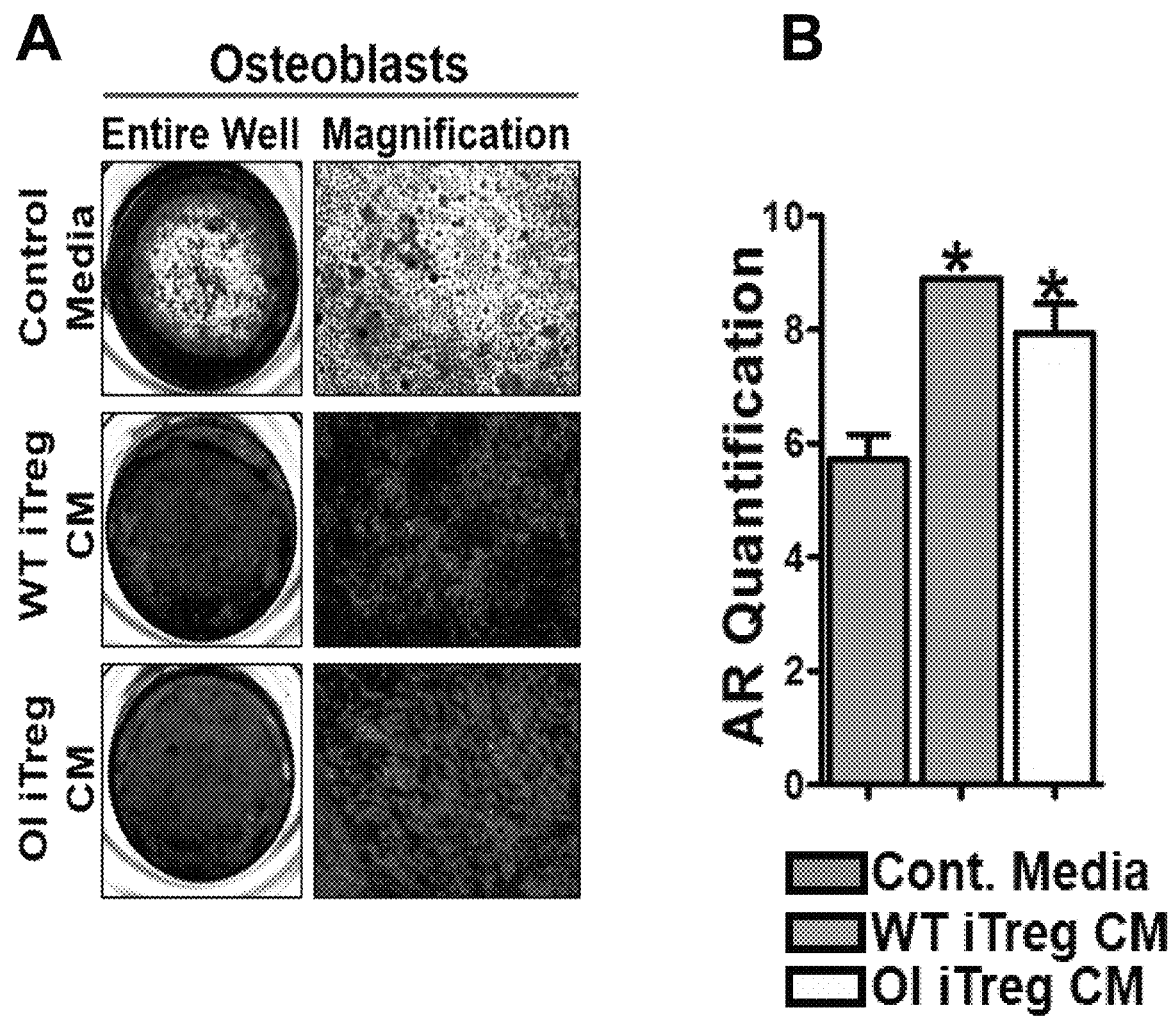
FIG. 12, comprising

In addition, the in vitro culture of oim calvarial cells with conditioned media (CM) from WT and OI iTregs caused increased mineralization. To obtain CM, after generating iTregs, the cells were washed and incubated with serum free media for 24 hours, which was then collected, centrifuged and stored at −80° C. until needed. To determine the effect of Tregs on osteogenesis, oim calvarial cells were cultured in osteogenic media ($\alpha$-MEM/15% FBS/ascorbic acid/$\beta$-glycerophosphate) supplemented with 50% CM from WT and OI iTregs. There was an increase in mineralization, as seen by alizarin red staining when the oim calvarial cells were treated with WT as well as OI iTreg CM as compared to cells grown with no CM. This increase was significant as is evident by quantification of the alizarin red staining. This indicates that iTregs have an effect on osteoblasts in OI and also that oim iTreg CM showed similar effects to WT iTreg CM. *$p<0.05$ WT and oim iTreg CM versus control media (FIG. 12).

Figure 13:
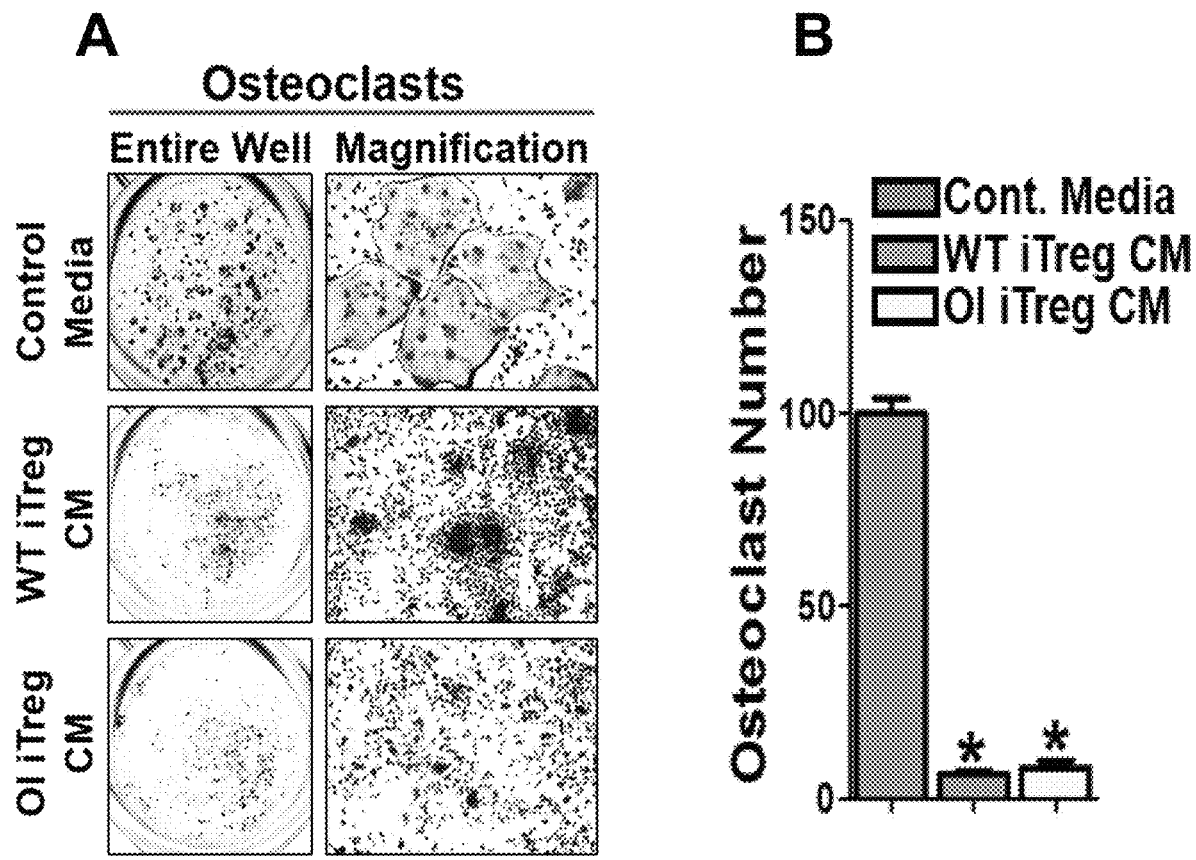
FIG. 13, comprising
Figure 14:
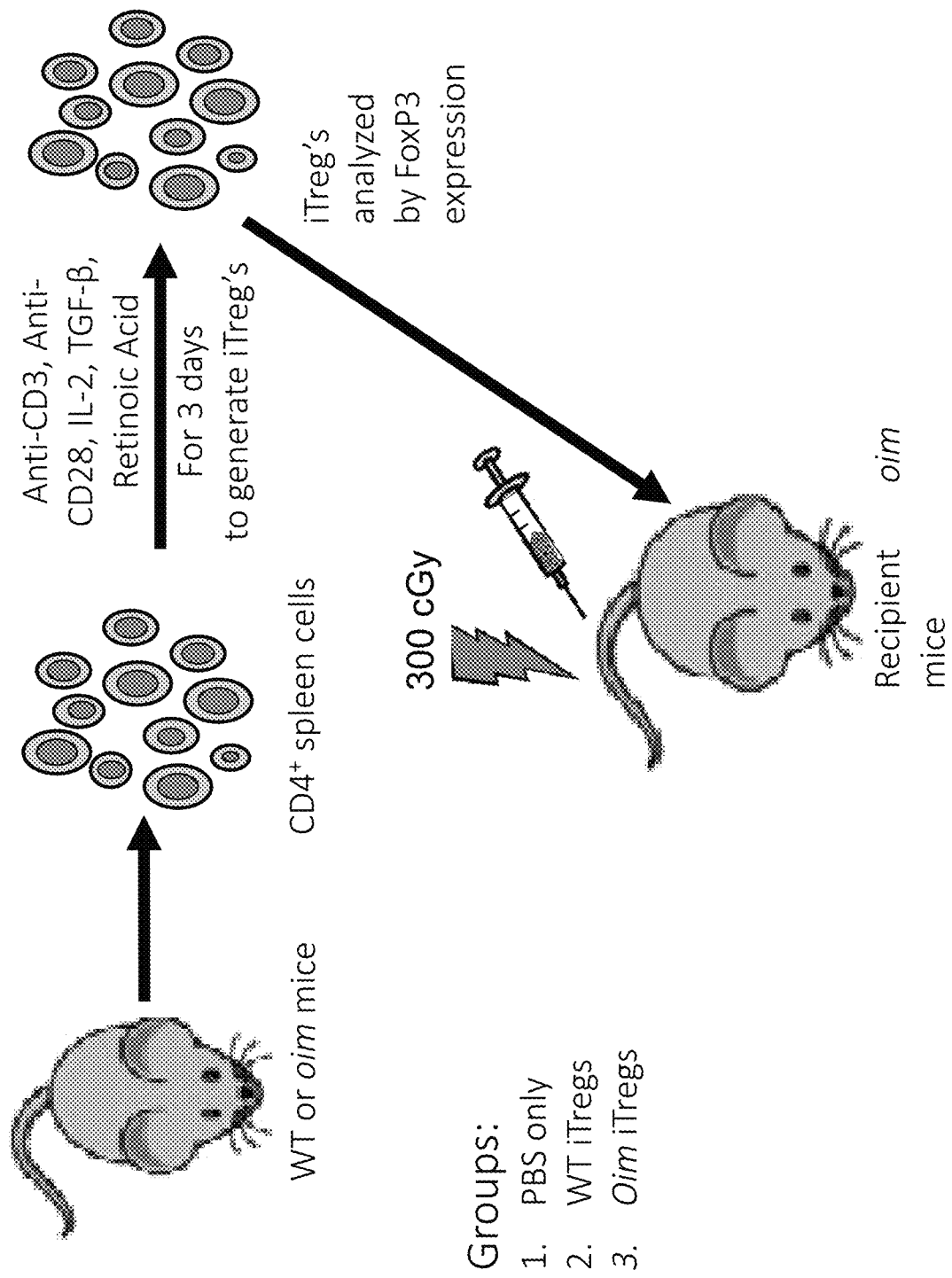
FIG. 14 is an illustration of the procedure for induced T regulatory Cell (iTreg) transplantation in oim mice alone without any BM cells. Recipients included the oim/oim model (B6C3Fe a/a-Col 1a2$^{oim}$/J), which resembles the type III severe, but nonlethal form of human OI. Donors included WT and oim mice. iTregs were obtained by culturing the CD4$^+$ spleen cells in a cocktail of anti-CD3 (5 µg/mL), anti-CD28 (5 µg/mL), IL-2 (100 U/mL), TGF-$\beta$ (5 ng/mL) and retinoic acid (40 nmol/mL) for 3 days. After 3 days, the cells were analyzed for FoxP3 expression to confirm the presence and the percentage of iTregs. iTregs alone from either WT or OI mice were transplanted into oim mice irradiated at 300 cGy. PBS injections in oim mice were used as control.
Figure 15:
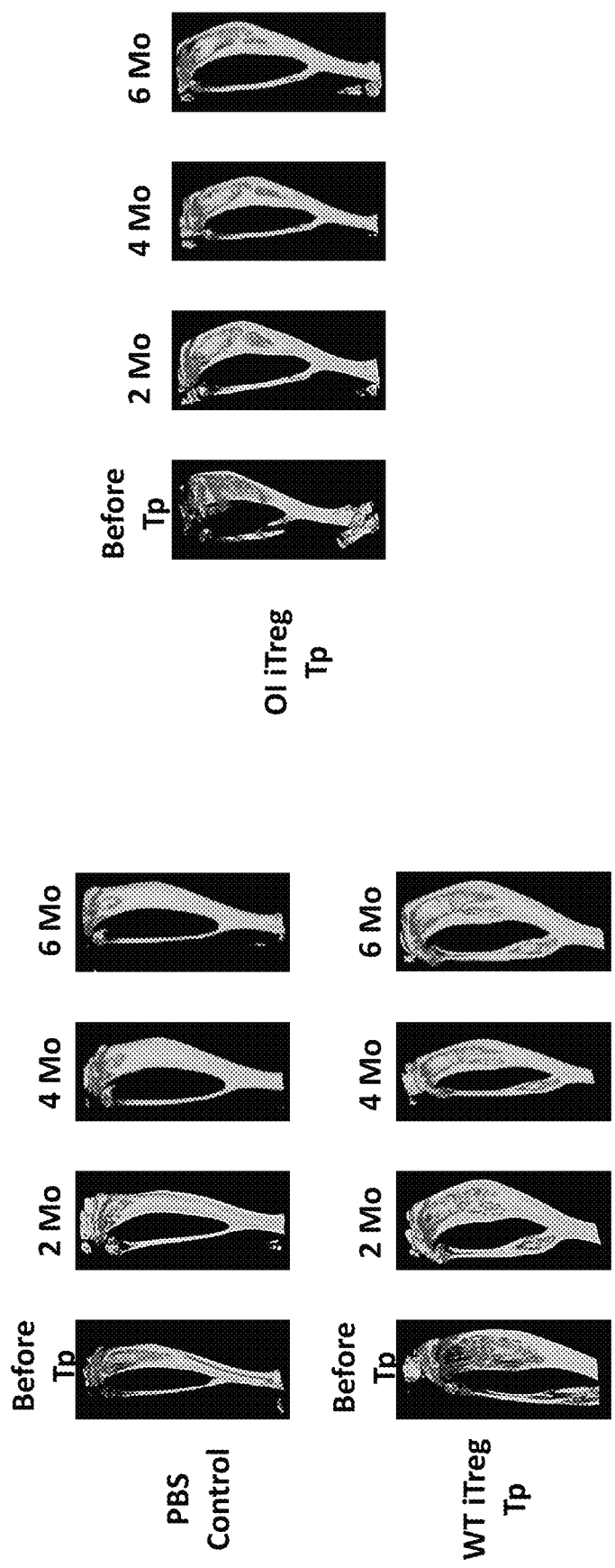
FIG. 15 is a series of images showing results from iTreg transplantation alone with 300 cGy of radiation. To determine if transplantation of iTregs alone would be beneficial, oim mice were transplanted with iTregs from WT and OI mice and the changes in bone morphology were tracked by Micro-CT 2,4 and 6 months after transplantation. There was a significant improvement in the bone architecture at 6 months compared to the before transplantation in OI bones transplanted with WT as well as OI iTregs.
Figure 16:
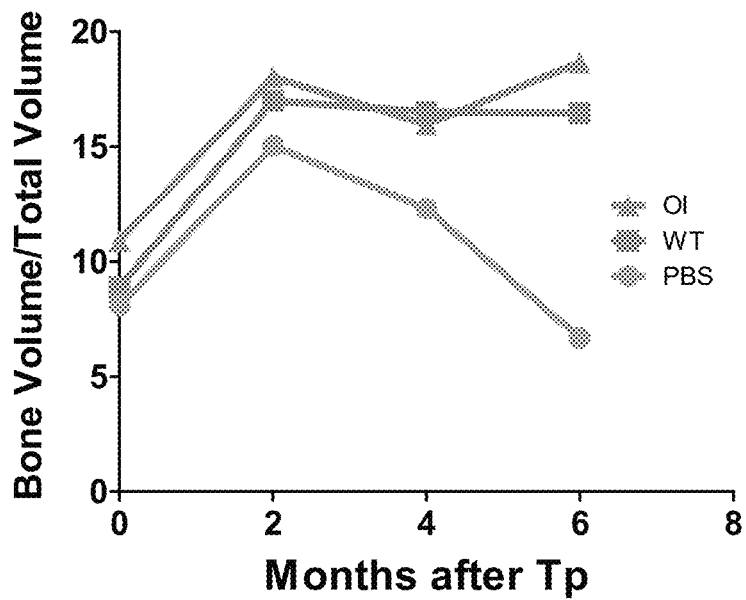
FIG. 16 is a series of images showing bone volume and fold increase following iTreg transplantation alone. On analysis of bone morphometric data, bone volume/total volume was increased in OI bones from mice transplanted with WT and OI iTregs as compared to PBS control at 2, 4 and 6 months after transplantation. On comparing the fold increase in bone volume/total volume the increase was seen in OI mice transplanted with OI iTregs only at 6 months after transplantation.
Figure 16:
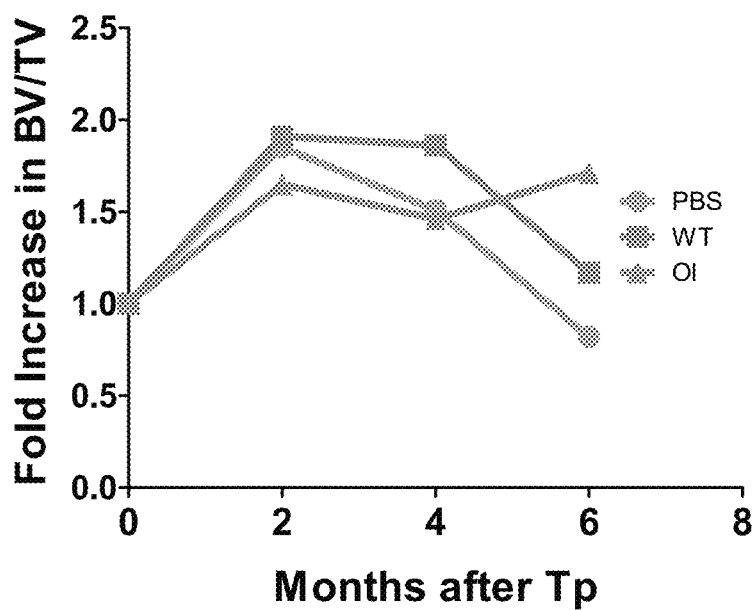
Figure 17:
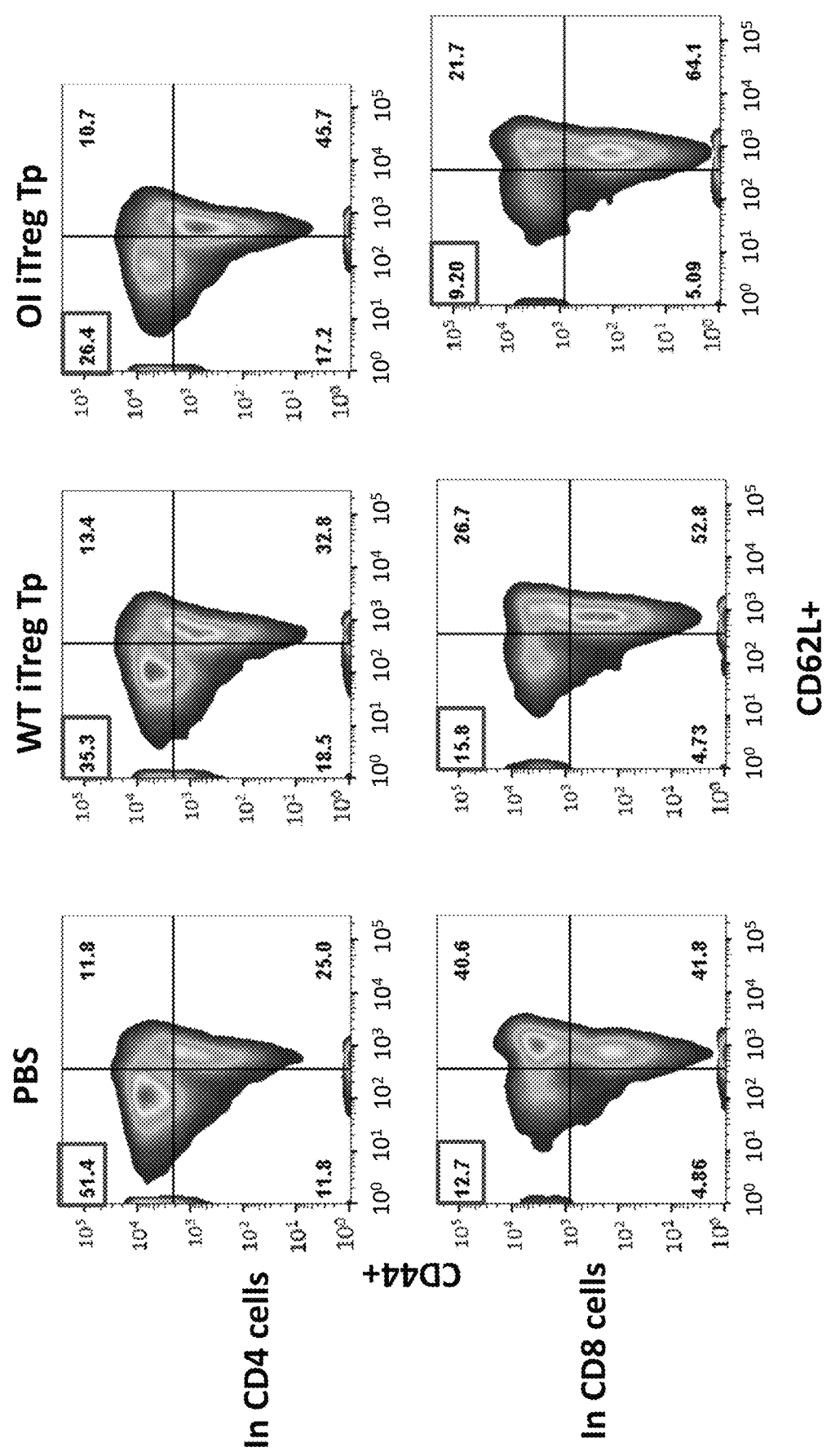
FIG. 17 is an image showing T cell activation in splenocytes following iTreg transplantation alone. OI mice transplanted with WT as well as OI iTregs, both show a decrease in the percentage of the activation molecule CD44 in CD4 as well as CD8 cells. This indicated a reduction in the activation state of the T cells after Treg transplantation.
Figure 18:
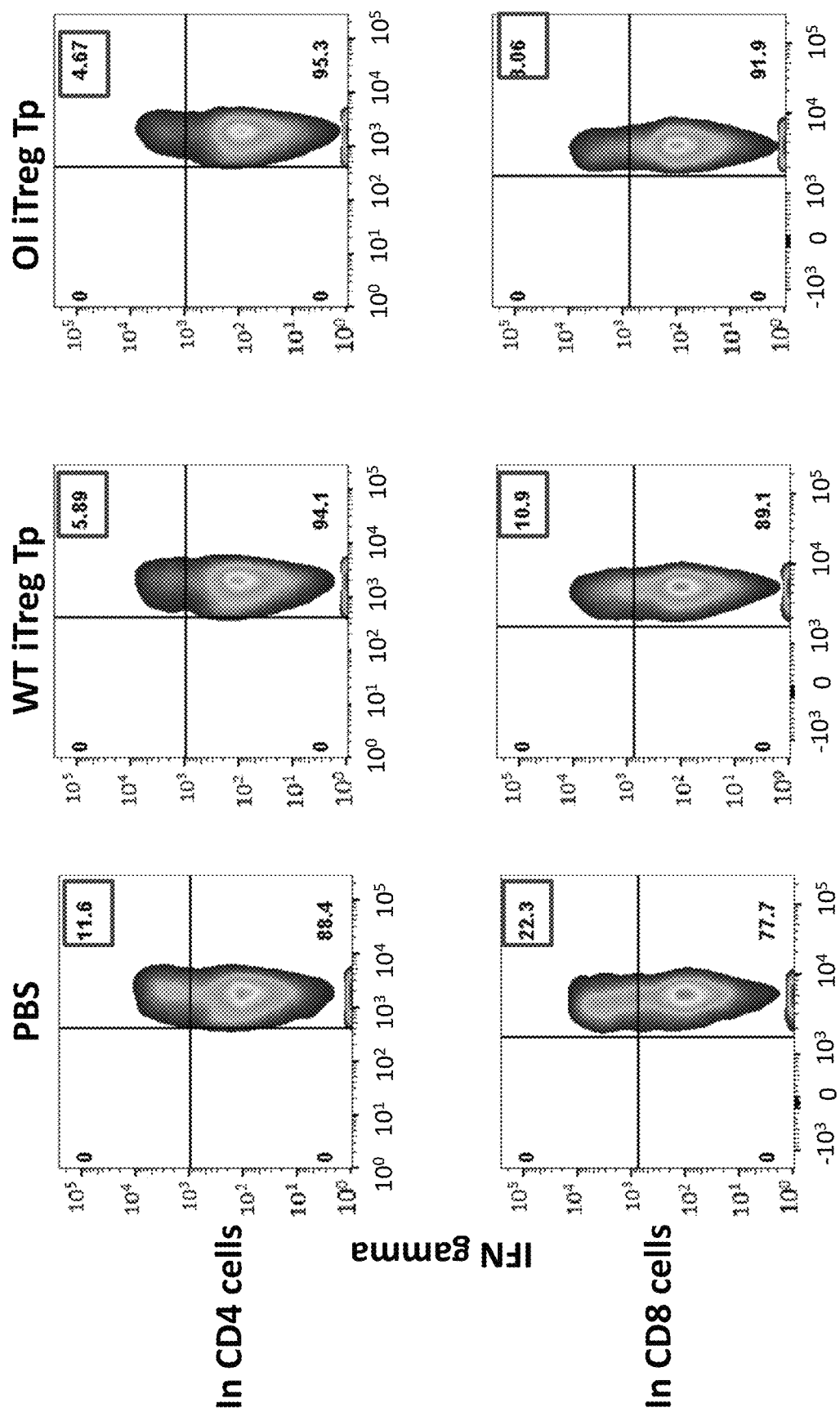
FIG. 18 is an image showing activation of cytokines in splenocytes following iTreg transplantation alone. The effector cytokine, IFN-$\gamma$ was significantly reduced in OI mice transplanted with iTregs from WT as well as OI mice. This again indicated a reduction in the activation state of the T cells after Treg transplantation.
Figure 19:
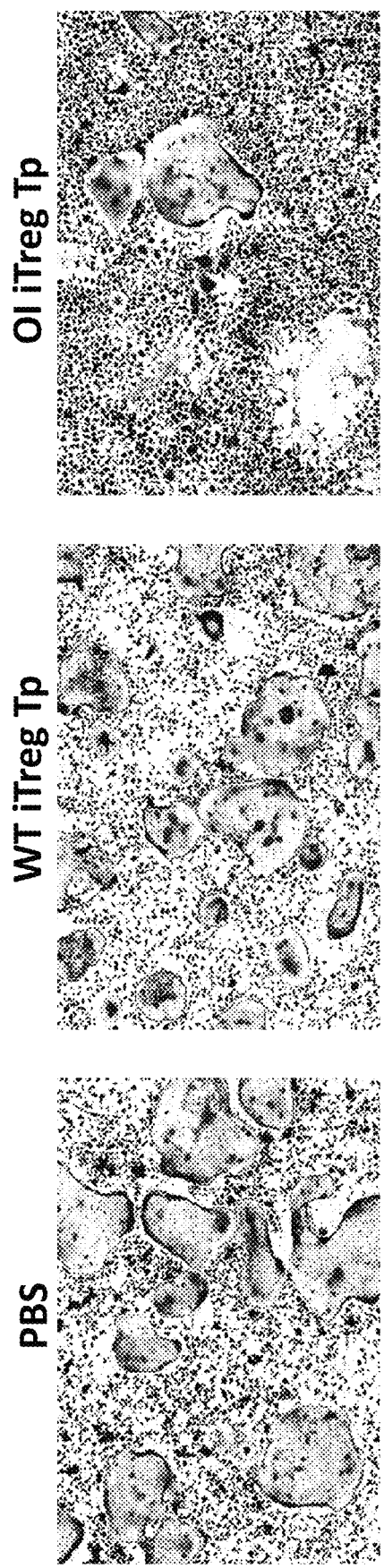
FIG. 19 is an image showing osteoclast number from bone marrow cells isolated from OI mice cultured under osteoclastic conditions. The number of osteoclasts formed was significantly reduced in the OI mice transplanted with iTregs from OI mice indicating a decrease in bone resorption in these mice, which can lead to a better bone architecture after iTreg transplantation.
Figure 20:
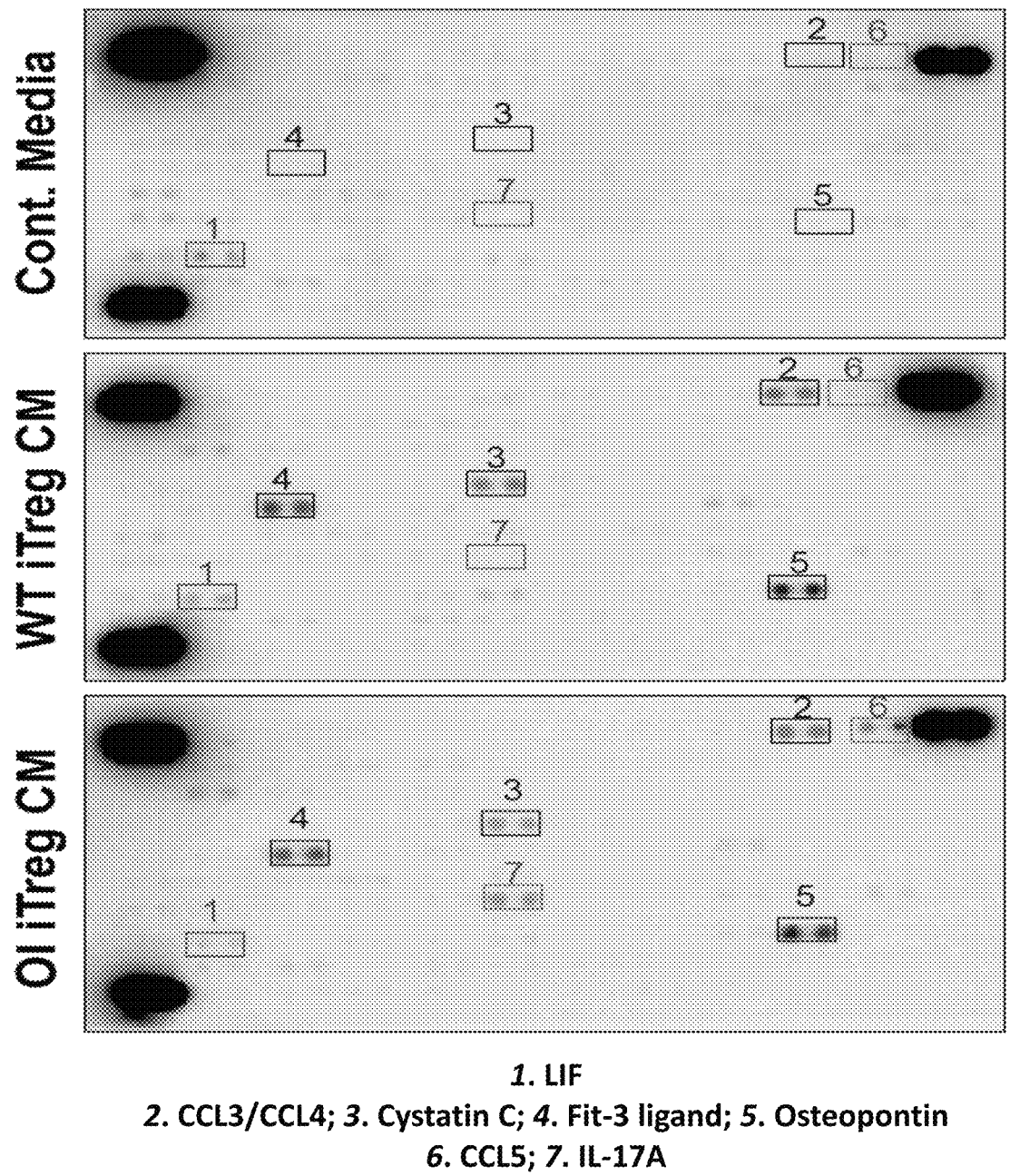
FIG. 20 is an image showing cytokine profile of WT and OI iTreg conditioned media. Media collected from WT and OI iTregs was analyzed by the Proteome Profiler Mouse cytokine XL array kit (R&D). Secretion of some factors such as CCL3/CCL4, Cystatin, Flt-3 ligand, and osteopontin were similarly increased in both WT and OI iTreg CM (blue). But some factors were differentially expressed in WT and OI iTreg CM. LIF was decreased in OI iTreg CM (red) while CC15 and IL-17A (green) were increased in OI iTreg CM compared to WT iTreg CM. These factors may play a role in the effect of iTregs in OI mice.

The in vitro culture of oim bone marrow cells for osteoclastogenesis with CM from iTregs reduces osteoclast number. To determine the effects of Tregs on osteoclastogenesis, BM was harvested from the tibia and femur of 4-5 week old oim mice. The cells were seeded into a 100 mm dish in $\alpha$-MEM with 10% FBS and incubated at 37° C. overnight. The supernatant was collected next day and centrifuged to collect the non-adherent BM cells, which were plated in 24 well dishes at $10 \times 10^6$ cells per well in $\alpha$-MEM/10% FBS/RANKL/M-CSF supplemented with 50% CM from WT and OI iTregs. The cells were stained for TRAP using leukocyte acid phosphatase kit to assess for formation of multinucleated TRAP$^+$ osteoclasts. There was a significant reduction in the number of osteoclasts formed when the BM cells were treated with CM from WT as well as OI iTregs, as seen both in the images and in the quantification of the osteoclast numbers. This indicates that iTregs have an effect on osteoclasts in OI and also that oim iTreg CM showed similar effects to WT iTreg CM. *$p<0.05$ WT and oim iTreg CM versus control media (FIG. 13).

SUMMARY

Oim mice display an activated T cell phenotype with increased secretion of IFN-$\gamma$ and TNF-$\alpha$. Reduced number of nTregs can be demonstrated in the oim mice compared to the WT mice. iTreg transplantation in oim mice results in enhanced clinical improvement (micro-CT) in oim mice transplanted with BM+iTregs (WT or OD as compared to oim mice transplanted with BM (WT or OI) only. Treating cells with WT and OI iTregs conditioned media demonstrates: an increase in the mineralization of oim calvarial osteoblasts, and a decrease in the osteoclastogenesis in oim BM cells.

Without wishing to be bound by any particular theory, quantitative restoration of the Treg compartment in OI would inhibit the higher pro-inflammatory cytokine secretion by endogenous T cells in OI, and lead to better bone formation. It is demonstrated herein that oim mice transplanted with bone marrow (BM)±iTregs (WT or OI), exhibited improvement in the trabecular parameters, and this improvement was enhanced when transplanted with BM+iTregs as compared to BM transplantation only. Thus, it is proposed that Treg transplantation (either alone or in combination with BM) can be used as a therapy for OI to reduce fracture rates, prevent bone deformities and lead to a better bone formation.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition for enhancing bone remodeling, or for treating osteogenesis imperfecta (OI), comprising at least one bone marrow (BM) cell, and at least one selected from the group consisting of: an induced T regulatory cell (iTreg), and iTreg conditioned medium (CM).

2. The composition of claim 1, wherein the iTreg is made by a method comprising incubating CD4$^+$ spleen cells with a composition comprising at least one selected from the group consisting of: anti-CD3 antibody, anti-CD28 antibody, IL-2, TGF-$\beta$, and retinoic acid.

3. The composition of claim 2, wherein the iTreg is made by a method comprising incubating CD4$^+$ spleen cells with a composition comprising anti-CD3 antibody, anti-CD28 antibody, IL-2, TGF-$\beta$, and retinoic acid.

4. The composition of claim 3, wherein the incubating step lasts for at least about three days.

5. The composition of claim 1, wherein the iTreg exhibits elevated expression of at least Foxp3.

6. The composition of claim 1, wherein the CM is made by a method comprising incubating one or more iTregs with serum free media.

7. The composition of claim 6, wherein the incubating step lasts for at least about 12 hours.

8. The composition of claim 1, further comprising at least one additional agent used to treat OI.

9. The composition of claim 8, wherein the additional agent comprises at least one agent selected from the group consisting of; a bisphosphonate, clomifene, raloxifene, tamoxifen, toremifene, bazedoxifene, lasofoxifene, ormeloxifene, Odanacatib, a Vitamin D analog, Denosumab, recombinant growth hormone, Romosozumab, Blosozumab, BSP804, Teriparatide, SD-208, ID11, Fresolimumab, and a combination thereof.

10. The composition of claim 9, wherein the bisphosphonate comprises at least one selected from the group consisting of: cholecalciferol, zoledronic acid, calcium carbonate, pamidronate, neridronate, olpadronate, alendronate, ibandronate, risedronate, zoledronate, etidronate, clodronate, and tiludronate.

11. A method for enhancing bone remodeling, or for treating a skeletal disease or disorder, comprising administering to a subject having a skeletal disease or disorder a composition comprising at least one selected from the group consisting of: an induced T regulatory cell (iTreg), and iTreg conditioned medium (CM).

12. The method of claim 11, further comprising the step of administering at least one BM cell to the subject.

13. The method of claim 11, further comprising the step of administering at least one additional agent used to treat the skeletal disease or disorder to the subject.

14. The method of claim 13, wherein the additional agent comprises at least one agent selected from the group consisting of: a bisphosphonate, clomifene, raloxifene, tamoxifen, toremifene, bazedoxifene, lasofoxifene, ormeloxifene, Odanacatib, a Vitamin D analog, Denosumab, recombinant growth hormone, Romosozumab, Blosozumab, BSP804, Teriparatide, SD-208, ID11, Fresolimumab, and a combination thereof.

15. The method of claim 14, wherein the bisphosphonate comprises at least one selected from the group consisting of: cholecalciferol, zoledronic acid, calcium carbonate, pamidronate, neridronate, olpadronate, alendronate, ibandronate, risedronate, zoledronate, etidronate, clodronate, and tiludronate.

16. The method of claim 11, wherein the skeletal disease or disorder is osteogenesis imperfecta (OI).

17. A composition for inducing the formation of iTregs, comprising anti-CD3 antibody present at a concentration of 5 μg/mL, anti-CD28 antibody present at a concentration of 5 μg/mL, IL-2 present at a concentration of 100U/mL, TGF-β present at a concentration of 5 ng/mL, and retinoic acid at a concentration of 40 nmol/mL.

* * * * *